(12) United States Patent
Howard et al.

(10) Patent No.: US 9,321,774 B2
(45) Date of Patent: Apr. 26, 2016

(54) PYRROLOBENZODIAZEPINES

(71) Applicant: MEDIMMUNE LIMITED, Cambridge, England (GB)

(72) Inventors: Philip Wilson Howard, London (GB); David Edwin Thurston, London (GB); Khondaker Mirazur Rahman, London (GB); Peter William Taylor, London (GB)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 14/397,843

(22) PCT Filed: Apr. 30, 2013

(86) PCT No.: PCT/GB2013/051097
§ 371 (c)(1),
(2) Date: Oct. 29, 2014

(87) PCT Pub. No.: WO2013/164592
PCT Pub. Date: Nov. 7, 2013

(65) Prior Publication Data
US 2015/0126495 A1    May 7, 2015

Related U.S. Application Data

(60) Provisional application No. 61/640,316, filed on Apr. 30, 2012.

(51) Int. Cl.
C07D 487/04 (2006.01)

(52) U.S. Cl.
CPC ................................ *C07D 487/04* (2013.01)

(58) Field of Classification Search
CPC ...................................................... C07D 487/04
See application file for complete search history.

(56) References Cited

U.S. PATENT DOCUMENTS

| | | | |
|---|---|---|---|
| 5,229,490 | A | 7/1993 | Tam |
| 6,187,797 | B1 | 2/2001 | Pruitt et al. |
| 6,562,806 | B1 | 5/2003 | Thurston et al. |
| 6,608,192 | B1 | 8/2003 | Thurston et al. |
| 6,613,787 | B2 | 9/2003 | Wilson et al. |
| 6,747,144 | B1 | 6/2004 | Thurston et al. |
| 6,909,006 | B1 | 6/2005 | Thurston et al. |
| 7,049,311 | B1 | 5/2006 | Thurston et al. |
| 7,067,511 | B2 | 6/2006 | Thurston et al. |
| 7,265,105 | B2 | 9/2007 | Thurston et al. |
| 7,407,951 | B2 | 8/2008 | Thurston et al. |
| 7,429,658 | B2 | 9/2008 | Howard et al. |
| 7,528,126 | B2 | 5/2009 | Howard et al. |
| 7,557,099 | B2 | 7/2009 | Howard et al. |
| 7,612,062 | B2 | 11/2009 | Howard et al. |
| 7,704,924 | B2 | 4/2010 | Thurston et al. |
| 7,741,319 | B2 | 6/2010 | Howard et al. |
| 2003/0195196 | A1 | 10/2003 | Thurston et al. |
| 2004/0092736 | A1 | 5/2004 | Thurston et al. |
| 2004/0138269 | A1 | 7/2004 | Sun et al. |
| 2004/0198722 | A1 | 10/2004 | Thurston et al. |
| 2007/0173497 | A1 | 7/2007 | Howard et al. |
| 2007/0185073 | A1 | 8/2007 | Howard et al. |
| 2007/0191309 | A1 | 8/2007 | Howard et al. |
| 2007/0191349 | A1 | 8/2007 | Howard et al. |
| 2007/0249591 | A1 | 10/2007 | Howard et al. |
| 2008/0090812 | A1 | 4/2008 | Pepper et al. |
| 2008/0167293 | A1 | 7/2008 | Howard et al. |
| 2008/0214525 | A1 | 9/2008 | Howard et al. |
| 2010/0113425 | A1 | 5/2010 | Howard et al. |
| 2011/0160192 | A1 | 6/2011 | Howard et al. |
| 2011/0162227 | A1 | 7/2011 | Howard et al. |

FOREIGN PATENT DOCUMENTS

| | | |
|---|---|---|
| JP | S5569587 | 5/1980 |
| JP | S58180487 | 10/1983 |
| WO | WO 98/28282 | 7/1998 |
| WO | WO 99/46244 | 9/1999 |
| WO | WO 00/12507 | 10/2000 |
| WO | WO 2005/085177 | 9/2005 |
| WO | WO 2006/111759 | 10/2006 |
| WO | WO 2007/039752 | 4/2007 |
| WO | WO 2009/060208 | 5/2009 |
| WO | WO 2010/010347 | 1/2010 |
| WO | WO 2010/043880 | 4/2010 |

OTHER PUBLICATIONS

Andersen, H.S. et al., "Discovery and SAR of a Novel Selective and Orally Bioavailable Nonpeptide Classical Competitive Inhibitor Class of Protein-Tyrosine Phosphatase 1B," J. Med. Chem., 2002, vol. 45, 4443-4459.

Antonow, D. et al.,"Parallel synthesis of a novel C2-aryl pyrrolo[2,1-c][1,4]benzodiazepine (PBD) library," J. Comb. Chem. (2007) 9:437-445.

Arima et al., "Studies on Tomaymycin, a New Antibiotic. I. Isolation and Properties of Tomaymycin," J. Antibiotics (1972) 25:437-444.

Baird, E.E. et al., "Solid phase synthesis of polyamides containing imidazole and pyrrole amino acids," J. Am. Chem. Soc. (1996) 118(26):6141-6146.

Banker, G.S. et al., Modern Pharmaceutics, Third Edition, Marcel Dekker, New York (1996) 451 and 596.

Baraldi, P.G. et al., "[2,1-c][1,4]benzodiazepine (PBD)-distamycin hybrid inhibits DNA binding to transcription factor Spl," Nucleotides and Nucleic Acids (2000) 19(8):1219-1229.

Baraldi, P.G. et al., "Design, synthesis and biological activity of a pyrrolo[2,1-c][1,4]benzodiazepine (PBD)-distamycin hybrid," Bioorganic & Medicinal Chemistry Letters, vol. 8, No. 21, 3019-3024 (1998).

Baraldi, P.G. et al., "Synthesis, in Vitro Antiproliferative Activity, and DNA-Binding Properties of Hybrid Molecules Containing Pyrrolo[2,1-c][1,4]benzodiazepine and Minor-Groove-Binding Oligopyrrole Carriers," J. Med. Chem., 42, 5131-5141 (1999).

Berge et al., "Pharmaceutical Salts," J. Pharm. Sci. (1977) 66:1-19.

Borgatti, M. et al , "Inhibition of NF-kB/DNA interactions and HIV-1 LTR directed transcription by hybrid molecules containing pyrrolo [2,1-c][1,4] benzodiazepine (PBD) and oligopyrrole carriers," Drug Development Research (2003) 60(3):173-185.

Bose et al., "New Approaches to Pyrrolo[2,1-c][1,4]benzodiazepines: Synthesis, DNA-binding and cytotoxicity of DC-81," Tetrahedron, 48, 751-758 (1992).

Briehn, C.A. et al., "Alternative heterocycles for DNA recognition: the benzimidazole/imidazole pair," Chem. Eur. J. (2003) 9:2110-2122.

Brucoli et al., "Novel C8-linked pyrrolobenzodiazepine (PBD)-heterocycle conjugates that recognize DNA sequences containing an inverted CCAAT box," Bioorganic and Medicinal Chemistry Letters, 21 (12), 3780-3783 (2011).

Damayanthi, Y. et al, Design and Synthesis of Novel Pyrrolo[2,1-c][1,4]benzodiazepine-Lexitropsin Conjugates, 64 J Org. Chem. 290 (1999).
Dangles, O. et al., "Selective Cleavage of the Allyl and Allyloxycarbonyl Groups through Palladium-Catalyzed Hydrostannolysis with Tributyltin Hydride. Application to the Selective Protection-Deprotection of Amino Acid Derivatives and in Peptide Synthesis," J. Org. Chem., 52, 4984-4993 (1987).
Dannley, R. L. et al., J. Am. Chem. Soc., 1954, vol. 76, 4543-4345.
Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.
Dorwald, F.Z., Side Reactions in Organic Synthesis: a Guide to Successful Synthesis Design, Weinheim: Wiley-VCH Verlag GmbH and Co., KGaA (2005) Preface.
Dupont, C. et al., "Synthesis of rhazinilam analogue acting as an inhibitor of tubulin assembly," Tetrahedron Lett. (2000) 41:5853-5856.
Edman, P. and Begg, G., "A Protein Sequenator," Eur. J. Biochem., 1, 80-91 (1967).
Fey, T. et al., "Silica-supported TEMPO catalyst: synthesis and application in the anelli oxidation of alcohols," J. Org. Chem. (2001) 66:8154-8159.
Firsching, A. et al., "Antiproliferative and angiostatic activity of suramin analogues," Cancer Res. (1995) 55:4957-4961.
Firth, J.D. et al., "Oxygen-regulated control elements in the phosphoglycerate kinase 1 and lactate dehydrogenase A genes: similarities with the erythropoietin 3' enhancer," Proc. Natl. Acad. Sci. USA (1994) 91:6496-6500.
Furka, A. et al., "Combinatorial libraries by portioning and mixing," Combin. Chem. & High Throughput Screening (1999) 2:105-122.
Furka, A. et al., "General method for rapid synthesis of multicomponent peptide mixtures," Int. J. Peptide Protein Res., 37, 487-493 (1991).
Gallop, M.A. et al., "Applications of combinatorial technologies to drug discovery. 1. Background and peptide combinatorial libraries," J. Med. Chem. (1994) 37(9):1233-1251.
Gavezzotti, A., "Are crystal structures predictable?" Acc. Chem. Res. (1994) 27:309-314.
Gordon, E.M. et al., "Applications of combinatorial technologies to drug discovery. 2. Combinatorial organic synthesis, library screening strategies, and future directions," J. Med. Chem. (1994) 37(10):1385-1401.
Greene, T. W. et al., Protective Groups in Organic Synthesis (2nd Ed) 1991, Ch 7, 315-345.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Hara et al., "DC 102, a new glycosidic pyrrolo(1,4)benzodiazepine antibiotic produced by *streptomyces* sp.", J. Antibiotics, 41, 702-704 (1988).
Hochlowski, J. et al., "Abbeymycin, a new anthramycin-type antibiotic produced by a streptomycete," J. Antibiotics, 40, 145-148 (1987).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem. (2009) in Press, 4 pages.
Hu, W-P. et al., "An efficient synthesis of pyrrolo[2,1-c][1,4]benzodiazepine. Synthesis of the antibiotic DC-81," J. Org. Chem. (2001) 66:2881-2883.
Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," Acc. Chem. Res., 19, 230-237 (1986).
Itoh et al., "Sibanomicin, a new pyrrolo(1,4)benzodiazepine antitumor antibiotic produced by a *micromonospora* sp." J. Antibiotics, 41, 1281-1284 (1988).
Jones, G.B. et al., "The non-covalent interaction of pyrrolo[2, 1-c][1,4]benzodiazepine-5, 11-diones with DNA," Anti-Cancer Drug Design (1990) 5:249-264.

Jordan, V.C., "Tamoxifen: a most unlikely pioneering medicine," Nature Reviews: Drug Discovery (2003) 2:205-213.
Kohn, K., "Anthramycin," Antibiotics III, Springer-Verlag, NY, 3-11 (1975).
Konishi, M. et al., "Chicamycin, a new antitumor antibiotic II. Structure determination of chicamycins A and B," J. Antibiotics, 37, 200-206 (1984).
Kumar, R. et al., "Design and synthesis of novel pyrrolo[2,1-c][1,4]benzodiazepine—imidazole containing polyamide conjugates," Heterocyclic Communications (2002) 81(1):19-26.
Kumar, R. et al., "Design, synthesis and in vitro cytotoxicity studies of novel pyrrolo [2,1][1,4]benzodiazepine-glycosylated pyrrole and imidazole polyamide conjugates," Org. Biomol. Chem. (2003) 1(19):3327-3342.
Kumar, R. et al., "Synthesis and antitumor cytotoxicity evaluation of novel pyrrolo[2,1-c][1,4]benzodiazepine imidazole containing polyamide conjugates," Oncology Research (2003) 13(4):221-233.
Kunimoto et al., "Mazethramycin, a new member of anthramycin group antibiotics," J. Antibiotics, 33, 665-667 (1980).
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Lescrinier, T. et al., "DNA-Binding Ligands from Peptide Libraries Containing Unnatural Amino Acids," Chem. Eur. J., 4, 3, 425-433 (1998).
Manzini, G. et al., "Interaction of diamidino-2-phenylindole (DAPI) with natural and synthetic nucleic acids," Nuc. Acids. Res. (1983) 11(24):8861-8876.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
McConnaughie, A.W. et al., "Novel acridine-triazenes as prototype combilexins: synthesis, DNA binding and biological activity," J. Med. Chem. (1995) 38:3488-3501.
Mischiati, C. et al., "Binding of hybrid molecules containing pyrrolo [2,1-c][1,4]benzodiazepine (PBD) and oligopyrrole carriers to the human immunodeficiency type 1 virus TAR-RNA," Biochem. Pharmacol. (2004) 67(3):401-410.
Nishiwaki, E. et al., "Efficient Synthesis of Oligo-N-Methylpyrrolecarboxamides and Related Compounds," Heterocycles, 1988, vol. 8, 1945-1952.
Paikoff, S.J. et al., "The Solid Phase Synthesis of N-Alkylcarbamate Oligomers", Tetrahedron Letters, 37, No. 32: 5653-5656 (1996).
Qian, Y. et al., "Biaryl Substituted Alkylboronate Esters as Thrombin Inhibitors," Bioorg. Med. Chem. Lett., 1997, vol. 7, No. 13, 1595-1600.
Rahman et al, J Med. Chem. (2013) 56(7) 2911-2935.
Rahman et al, J. Antimicrob. Chemother. (2012) 67 (7): 1683-1696.
Rahman et al., Chem. Comms., 2009 (No. 27), 4097-4099.
Reddy et al., "Design, synthesis and in vitro cytotoxicity studies of novel pyrrolo[2,1-c][1,4]benzodiazepine (PBD)-polyamide conjugates and 2,2'-PBD dimers," Anti-Cancer Drug Design (2000) 15(3):225-238.
Renneberg et al., "Imidazopyridine/Pyrrole and Hydroxybenzimidazole/Pyrrole Pairs for DNA Minor Groove Recognition," J. Am. Chem. Soc., 2003, vol. 125, 5707-5716.
Shimizu, K et al., "Prothracarcin, a Novel Antitumor Antibiotic," J. Antibiotics, 35, 972-978 (1982).
Soth, M.J. and Nowick, J.S., "Unnatural oligomers and unnatural oligomer libraries", Curr. Opin. Chem. Biol., 1:120-129 (1997).
Souillac, P. et al., "Characterization of delivery systems, differential scanning calorimetry," Encyclopedia of Controlled Drug Delivery (1999) 212-227.
Takeuchi, T. et al., "Neothramycins A and B, New Antitumor Antibiotics," J. Antibiotics, 29, 93-96 (1976).

Tercel, M. et al., "Unsymmetrical DNA cross-linking agents: combination of the CBI and PBD pharmacophores," J. Med. Chem. (2003) 46:2132-2151.
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Topiol, S. et al., "Computer aided analysis of split and mix combinatorial libraries," J. Comb. Chem. (2001) 3:20-27.
Tsunakawa, M. et al., "Porothramycin, a new antibiotic of the anthramycin group: Production, isolation, structure and biological activity," J. Antibiotics, 41:1366-1373 (1988).
Vippagunta, S.R. et al., "Crystalline solids," Adv. Drug Delivery Rev. (2001) 48:3-26.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wells, G. et al., "Pyrrolobenzodiazepine-polyamide libraries: synthesis and DNA binding selectivity," Proc. Am. Assoc. Canc. Res. (2003) 44:85-86, #452.
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons, New York (1995) 975-977.
Woods, C.R. et al., "Synthesis and DNA binding properties of iminodiacetic acid-linked polyamides: characterization of cooperative extended 2:1 side-by-side parallel binding," J. Am. Chem. Soc. (2002) 124:10676-10682.
Xie, G. et al, Bisindolylmaleimides Linked to DNA Minor Groove Binding Lexitropsins: Synthesis, Inhibitory Activity Against Topoisomerase I, and Biological Evaluation, 39 J Med. Chem. 1049 (1996).
Xie, G. et al., "Bisindolylmaleimides linked to DNA minor groove binding lexitropsins: synthesis, inhibitory activity against topoisomerasel, and biological evaluation," J. Med. Chem., 1996, vol. 39, 1049-1055.

(Continued)

*Primary Examiner* — Bruck Kifle

(74) *Attorney, Agent, or Firm* — Michael Best & Friedrich LLP

(57) ABSTRACT

A compound of formula (I) or a salt or solvate thereof, wherein the dotted double bond indicates the presence of a single or double bond between C2 and C3; $R^2$ is selected from —H, —OH, =O, =CH$_2$, —CN, —R, OR, halo, dihalo, =CHR, =CHRR', —O—SO$_2$—R, CO$_2$R and COR; $R^7$ is selected from H, R, OH, OR, SH, SR, NH$_2$, NHR, NRR', nitro, Me$_3$Sn and halo; where R and R' are independently selected from optionally substituted $C_{1-7}$ alkyl, $C_{3-20}$ heterocyclyl and $C_{5-20}$ aryl groups; $R^{10}$ and $R^{11}$ either together form a double bond, or are selected from H and QR$^Q$ respectively, where Q is selected from O, S and NH and $R^Q$ is H or $C_{1-7}$ alkyl or H and SO$_x$M, where x is 2 or 3, and M is a monovalent pharmaceutically acceptable cation; A is selected from (A1), (A2), (A3), (A4) or (A5) where $X^1$ and $Y^1$ are selected from: CH and NH; CH and NMe; N and NMe; CH and S; N and S; N and O; and CH and O, respectively; $X^2$ and $Y^2$ are selected from: CH and NH; CH and NMe; N and NMe; CH and S; N and S; N and O; and CH and O, respectively; $Z^1$ is selected from O and S; $Z^2$ is selected from CH and N; F is selected from a single bond and -(E-F$^1$)$_m$—; each E is independently selected from a single bond, and —C(=O)—NH—; each $F^1$ is independently a $C_{3-20}$ heteroarylene group; m is 1, 2 or 3; G is selected from hydrogen, $C_{1-4}$alkyl, —C(=O)—O—$C_{1-4}$alkyl, —(CH$_2$)$_n$—$C_{3-20}$ heterocycloalkyl, and —O—(CH$_2$)$_n$—$C_{3-20}$ heterocycloalkyl group; each n is 0-4; provided that A2 is not A2', where $X^1$ and $Y^1$ of A2' are selected from: CH and NH; CH and NMe; COH and NMe; CH and S; N and NMe; N and S, respectively; and provided that A3 is not A3', where $X^2$ and $Y^2$ of A3' are selected from: CH and NMe; COH and NMe; CH and S; N and NMe; N and S, respectively; B is either a single bond or (B1), where X and Y of B1 are selected from: CH and NMe; COH and NMe; CH and S; N and NMe; N and S, respectively; and $R^1$ is $C_{1-4}$ alkyl.

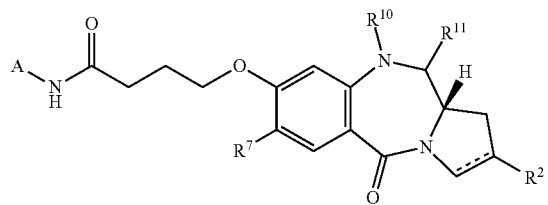

(I)

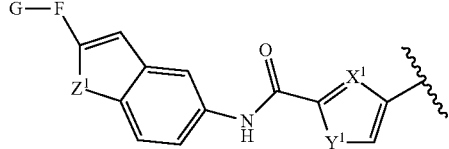

(A1)

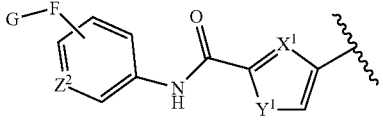

(A2)

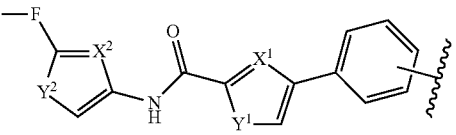

(A3)

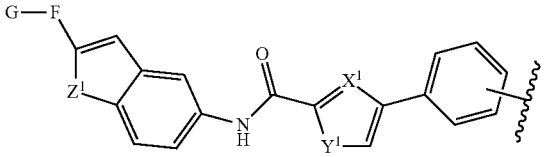

(A4)

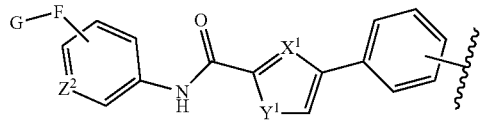

(A5)

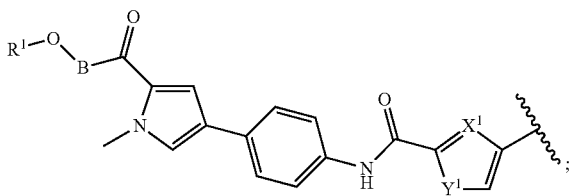

(A2')

-continued
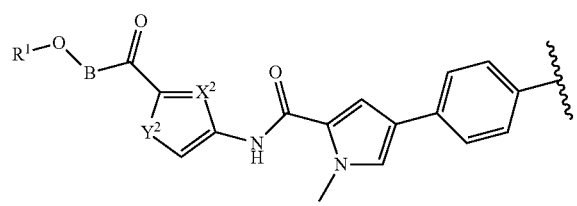
(A3′)
-continued
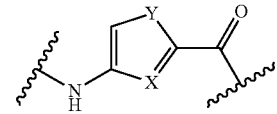
(B1)
20 Claims, No Drawings

PYRROLOBENZODIAZEPINES

CROSS-REFERENCE TO RELATED APPLICATIONS

This application is a national stage filing under 35 U.S.C. 371 of International Application No. PCT/GB2013/051097 filed Apr. 30, 2013, and claims the benefit of U.S. Provisional Application No. 61/640,316 filed Apr. 30, 2012, which is incorporated by reference herein.

The present invention relates to pyrrolobenzodiazepines (PBDs) and in particular to PBD monomers and methods of synthesising PBD monomers.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 35, 972-978 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

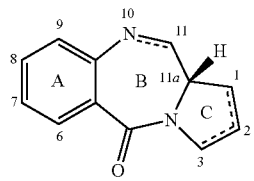

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents. The synthesis of the compounds has been reviewed in Thurston, D. E., et al., *Chem. Rev.*, 1994, 94, 433-465 and Thurston, D. E., et al., *Chem. Rev.*, 2011, 111, 2815-2864.

The large majority of antibiotics in current clinical use are derived from bactericidal or bacteriostatic molecules produced as secondary metabolites by microbes, predominantly those belonging to the moulds and actinobacteria. Screening has identified molecules such as the pyrrolobenzodiazepines (PBDs) tomaymycin, anthramycin and DC-81 that exerted potent antibacterial activity against human pathogens through a capacity to bind to DNA; some of these compounds have potential as cancer chemotherapeutics but a high degree of cytotoxicity has rendered them unattractive as antibacterial antibiotics in comparison to other classes of compound.

However, the evolution of multidrug-resistant pathogens capable of rapid and efficient horizontal transmission of genes encoding antibiotic resistance determinants has facilitated the erosion in a relatively short timeframe of much of the therapeutic value of frontline antibacterial chemotherapeutic agents. Increasing multidrug resistance in Gram-negative pathogens such as *Pseudomonas aeruginosa* and *Acinetobacter baumannii* has forced the reappraisal of colistin for systemic use; this polymyxin antibiotic, discovered more than fifty years ago and until recently considered too toxic for non-topical use, is now widely used systemically due to the limited therapeutic options available for these infections.

A number of conjugates of PBD with pyrroles and imidazoles have been reported, such as:

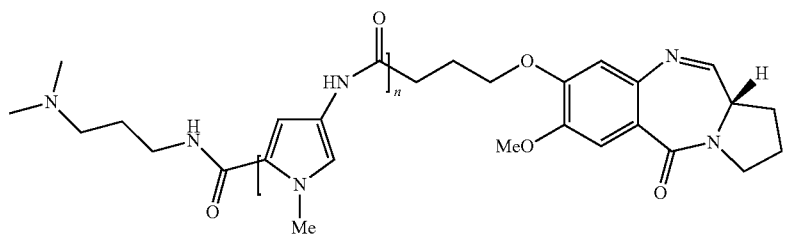

where n=1-3 (Damayanthi, Y., et al., *Journal of Organic Chemistry*, 64(1), 290-292 (1999));

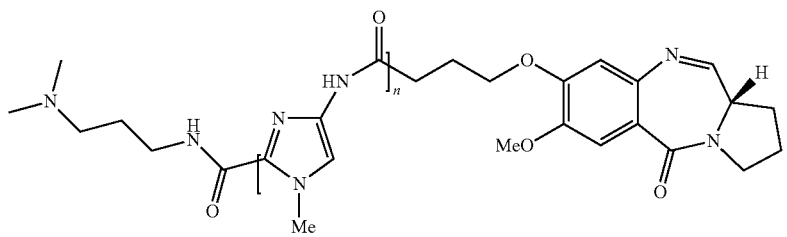

where n=1-3 and

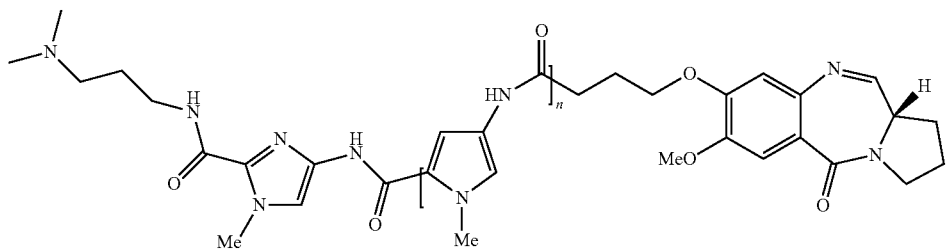

where n=1-2 (Kumar, R. and Lown, J. W. *Oncology Research*, 13(4), 221-233 (2003)); Kumar, R., et al., *Heterocyclic Communications*, 8(1), 19-26 (2002));

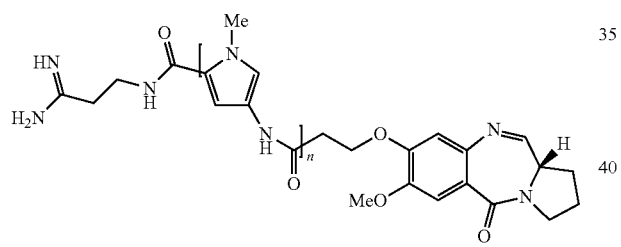

where n=1-4, (Baraldi, P. G., et al., *Journal of Medicinal Chemistry*, 42(25), 5131-5141 (1999));

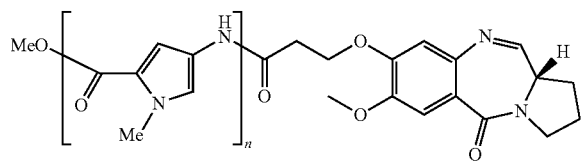

where n=3, (Wells, G., et al., *Proc. Am. Assoc. Canc. Res.*, 2003, 44, 452).

In WO 2005/085177, some of the present inventors disclosed amino acids comprising a biaryl core that could have useful properties in DNA binding.

The inventors have now discovered that the PBD conjugates of the prior art may be modified in order to achieve improved properties, particularly antibacterial properties. In particular, the present invention relates to the incorporation of an amino acid residue containing a 5-membered heterocyclic group in combination with an arylene based amino acid residue in a PBD conjugate results in highly effective compounds.

A first aspect of the present invention provides a compound of formula I:

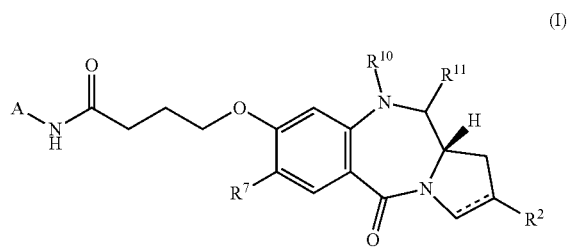

or a salt or solvate thereof, wherein:

the dotted double bond indicates the presence of a single or double bond between C2 and C3;

$R^2$ is selected from —H, —OH, =O, =CH$_2$, —CN, —R, OR, halo, dihalo, =CHR, =CHRR', —O—SO$_2$—R, CO$_2$R and COR;

$R^7$ is selected from H, R, OH, OR, SH, SR, NH$_2$, NHR, NRR', nitro, Me$_3$Sn and halo; where R and R' are independently selected from optionally substituted C$_{1-7}$ alkyl, C$_{3-20}$ heterocyclyl and C$_{5-20}$ aryl groups;

$R^{10}$ and $R^{11}$ either together form a double bond, or are selected from H and QR$^Q$ respectively, where Q is selected from O, S and NH and R$^Q$ is H or C$_{1-7}$ alkyl or H and SO$_x$M, where x is 2 or 3, and M is a monovalent pharmaceutically acceptable cation;

A is selected from A1, A2, A3, A4 or A5:

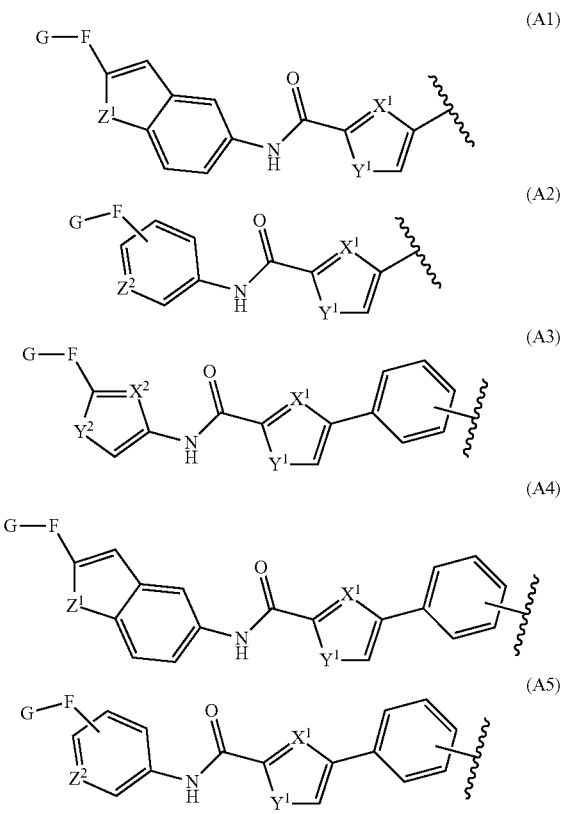

Where
X¹ and Y¹ are selected from: CH and NH; CH and NMe; N and NMe; CH and S; N and S; N and O; and CH and O, respectively;
X² and Y² are selected from: CH and NH; CH and NMe; N and NMe; CH and S; N and S; N and O; and CH and O, respectively;
Z¹ is selected from O and S;
Z² is selected from CH and N;
F is selected from a single bond and -(E-F¹)$_m$—;
each E is independently selected from a single bond, and —C(=O)—NH—;
each F¹ is independently a $C_{3-20}$ heteroarylene group;
m is 1, 2 or 3;
G is selected from hydrogen, $C_{1-4}$alkyl, —C(=O)—O—$C_{1-4}$alkyl, —(CH$_2$)$_n$—$C_{3-20}$ heterocycloalkyl, and —O—(CH$_2$)$_n$—$C_{3-20}$ heterocycloalkyl group, and each n is 0-4;
provided that A2 is not A2':

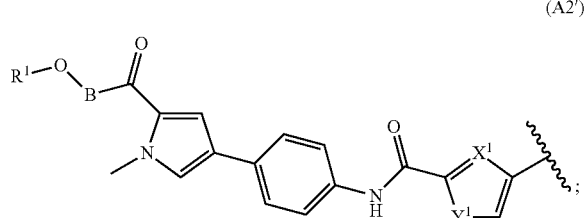

where X¹ and Y¹ of A2' are selected from: CH and NMe; COH and NMe; CH and S; N and NMe; N and S, respectively; and provided that A3 is not A3':

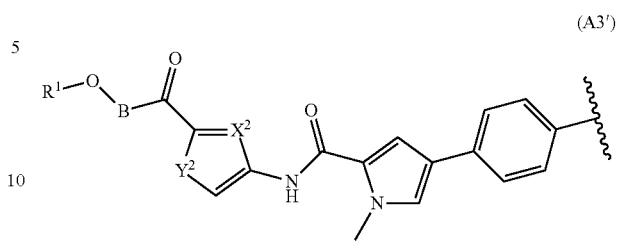

where X² and Y² of A3' are selected from: CH and NMe; COH and NMe; CH and S; N and NMe; N and S, respectively; B in A2' and A3' is either a single bond or:

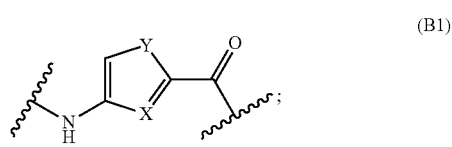

where X and Y of B1 are selected from: CH and NMe; COH and NMe; CH and S; N and NMe; N and S, respectively; and R¹ is $C_{1-4}$ alkyl.

A second aspect of the present invention provides a method of synthesis of a compound of formula I.

A third aspect of the present invention provides a pharmaceutical composition comprising a compound of the first aspect of the invention and a pharmaceutically acceptable carrier or diluent.

A fourth aspect of the present invention provides a compound of the first aspect of the invention for use in a method of therapy.

A fifth aspect of the present invention provides the use of a compound of the first aspect of the invention in the manufacture of a medicament for the treatment of a bacterial infection. This aspect also provides a compound of the first aspect for use in a method of treatment of a bacterial infection.

A sixth aspect of the present invention provides a method of treatment of a patient suffering from a bacterial infection, comprising administering to said patient a therapeutically acceptable amount of a compound of the first aspect or a composition of the third aspect.

In the fourth to sixth aspects of the invention, the compound of the invention may be administered alone or in combination with other treatments, either simultaneously or sequentially dependent upon the condition to be treated. In the third aspect of the invention, the pharmaceutical composition may comprise one or more (e.g. two, three or four) further active agents.

DEFINITIONS

Substituents

The phrase "optionally substituted" as used herein, pertains to a parent group which may be unsubstituted or which may be substituted.

Unless otherwise specified, the term "substituted" as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-7}$ alkyl: The term "$C_{1-7}$ alkyl" as used herein, pertains to a monovalent moiety obtained by removing a hydrogen atom from a carbon atom of a hydrocarbon compound having from 1 to 7 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-7}$ Alkenyl: The term "$C_{2-7}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

$C_{2-7}$ alkynyl: The term "$C_{2-7}$ alkynyl" as used herein, pertains to an alkyl group having one or more carbon-carbon triple bonds.

Examples of unsaturated alkynyl groups include, but are not limited to, ethynyl (ethinyl, —C≡CH) and 2-propynyl (propargyl, —CH$_2$—C≡CH).

$C_{3-7}$ cycloalkyl: The term "$C_{3-7}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atoms from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$); $N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($C_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($C_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($C_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The terms "arylene", "carboarylene", "heteroarylene" as used herein, pertain to a divalent moiety obtained by removing a hydrogen atom from each of two ring atoms of a aromatic compound as described above with reference to aryl, carboaryl and heteroaryl.

The above groups, whether alone or part of another substituent, may themselves optionally be substituted with one or more groups selected from themselves and the additional substituents listed below.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.
Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).
Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).
Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to —CH(OH)(OMe) and —CH(OH)(OEt).
Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).
Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).
Oxo (keto, -one): =O.
Thione (thioketone): =S.
Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.
Formyl (carbaldehyde, carboxaldehyde): —C(=O)H.
Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).
Carboxy (carboxylic acid): —C(=O)OH.
Thiocarboxy (thiocarboxylic acid): —C(=S)SH.
Thiolocarboxy (thiolocarboxylic acid): —C(=O)SH.
Thionocarboxy (thionocarboxylic acid): —C(=S)OH.
Imidic acid: —C(=NH)OH.
Hydroxamic acid: —C(=NOH)OH.
Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.
Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.
Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.
Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$ aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

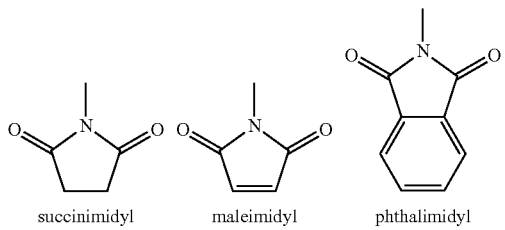

succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R')CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

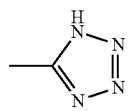

Imino: =NR, wherein R is an imino substituent, for example, for example, hydrogen, a C$_{1-7}$ alkyl group, a C$_{3-20}$ heterocyclyl group, or a C$_{5-20}$ aryl group, preferably H or a C$_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a C$_{1-7}$ alkyl group (also referred to as a C$_{1-7}$alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Disulfide: —SS—R, wherein R is a disulfide substituent, for example, a C$_{1-7}$ alkyl group, a C$_{3-20}$ heterocyclyl group, or a C$_{5-20}$ aryl group, preferably a C$_{1-7}$ alkyl group (also referred to herein as C$_{1-7}$ alkyl disulfide). Examples of C$_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a C$_{1-7}$ alkyl group, a C$_{3-20}$ heterocyclyl group, or a C$_{5-20}$ aryl group, preferably a C$_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group, including, for example, a fluorinated or perfluorinated C$_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$O$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$ alkyl group, a C$_{3-20}$ heterocyclyl group, or a C$_{5-20}$ aryl group, preferably a C$_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^{22}$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^{22}$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Nitrogen Protecting Groups

Nitrogen protecting groups are well known in the art. Preferred nitrogen protecting groups are carbamate protecting groups that have the general formula:

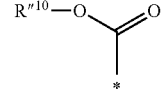

A large number of possible carbamate nitrogen protecting groups are listed on pages 706 to 771 of Wuts, P. G. M. and Greene, T. W., Protective Groups in Organic Synthesis, 4$^{th}$ Edition, Wiley-Interscience, 2007, which is incorporated herein by reference.

Particularly preferred protecting groups include Alloc, Troc, Teoc, BOC, Doc, Hoc, TcBOC, Fmoc, 1-Adoc and 2-Adoc.

Hydroxyl Protecting Groups

Hydroxyl protecting groups are well known in the art. A large number of suitable groups are described on pages 16 to 366 of Wuts, P. G. M. and Greene, T. W., Protective Groups in Organic Synthesis, 4$^{th}$ Edition, Wiley-Interscience, 2007, which is incorporated herein by reference.

Classes of particular interest include silyl ethers, methyl ethers, alkyl ethers, benzyl ethers, esters, benzoates, carbonates, and sulfonates.

Particularly preferred protecting groups include THP.

Bacterial Infections and Infectious Diseases

One of ordinary skill in the art is readily able to determine whether or not a candidate compound treats a bacterial infection or bacterial infectious disease. For example, assays which may conveniently be used to assess the activity offered by a particular compound are described in the examples below.

The term "bacterial infection" pertains to an invasion of body tissues by bacteria, their multiplication and the reaction of body tissues to the bacteria and the toxins that they produce. The term "bacterial infectious disease" pertains to a disease caused by bacteria.

Examples of bacterial infections and infectious bacterial diseases include, but are not limited to, hospital- and community acquired infections due to Gram-positive bacteria such as *Staphylococcus aureus*, including multi-drug resistant forms such as methicillin-resistant *S. aureus* (MRSA), and to streptococci, including drug resistant forms such as vancomycin-resistant enterococci (VRE). Other infections that could be treated include those due to *Clostridium difficile, Listeria monocytogenes* and skin infections due to Gram-positive bacteria.

Preferrably the compounds of the present invention are useful in the treatment of bacterial infections infectious bacterial diseases caused by bacterial infections involving drug resistant bacterial strains. Particularly preferred bacterial strains are *Staphylococcus aureus*.

Preferably, the treatment is of a bacterial infectious disease or bacterial infection involving MRSA, vancomycin-intermediate *S. aureus* (VISA), vancomycin-resistant *S. aureus* (VRSA) and other infections due to drug resistant Gram-positive bacteria.

Methods of Treatment

As described above, the present invention provides the use of a compound of the first aspect of the invention in a method of therapy.

The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated. Examples of treatments and therapies include, but are not limited to, β-lactam drugs such as the penicillins and cephalosporins, aminoglycosides, fluoroquinolones, oxazolidinones and the streptogramins.

Pharmaceutical compositions according to the present invention, and for use in accordance with the present invention, may comprise, in addition to the active ingredient, i.e. a compound of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Dosage

It will be appreciated by one of skill in the art that appropriate dosages of the compound can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

For the prevention or treatment of disease, the appropriate dosage of the compound of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of compound to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of a compound. Other dosage regimens may be useful. The progress of this therapy is easily monitored by conventional techniques and assays.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N+HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Preferably compounds of the present invention have the following stereochemistry at the C11 position:

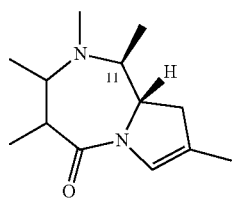

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

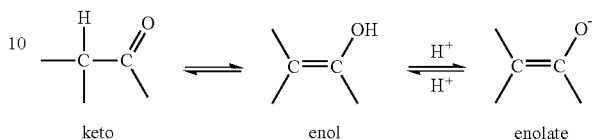

keto      enol      enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO⁻), then a salt may be formed with a suitable cation. Examples of suitable inorganic cations include, but are not limited to, alkali metal ions such as Na⁺ and K⁺, alkaline earth cations such as $Ca^{2+}$ and $Mg^{2+}$, and other cations such as $Al^{3+}$. Examples of suitable organic cations include, but are not limited to, ammonium ion (i.e. $NH_4^+$) and substituted ammonium ions (e.g. $NH_3R^+$, $NH_2R^{2+}$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Compounds of formula I include compounds where a nucleophilic solvent ($H_2O$, $R^A OH$, $R^A NH_2$, $R^A SH$) adds across the imine bond of the PBD moiety, which is illustrated below where the solvent is water or an alcohol ($R^A OH$, where $R^A$ is an ether substituent as described above):

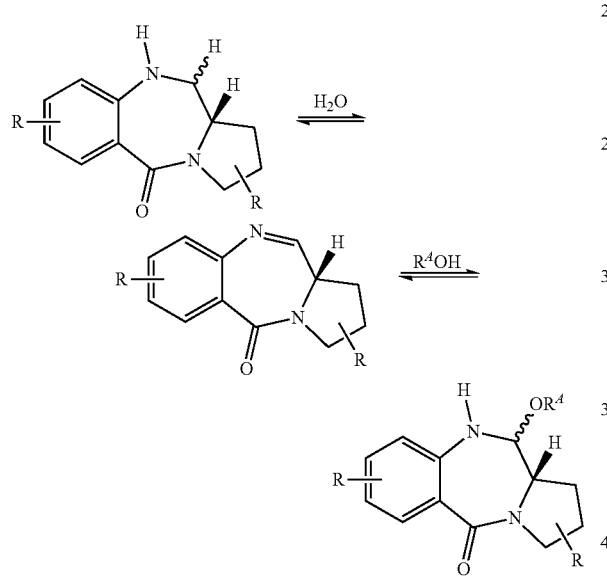

These forms can be called the carbinolamine and carbinolamine ether forms of the PBD. The balance of these equilibria depend on the conditions in which the compounds are found, as well as the nature of the moiety itself.

These compounds may be isolated in solid form, for example, by lyophilisation.

General Synthetic Routes

Compounds of formula I where $R^{10}$ and $R^{11}$ together form a double bond may be synthesised from compounds of formula 2:

(2)

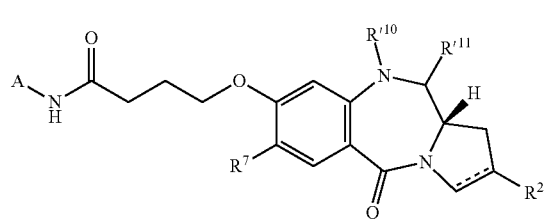

$R'^{10}$ is a nitrogen protecting group and $R'^{11}$ is O—$R^{12}$, wherein $R^{12}$ is H or a hydroxyl protecting group. Such techniques are well known in the art, and are described, for example, in Wuts, P. G. M. and Greene, T. W., Protective Groups in Organic Synthesis, 4$^{th}$ Edition, Wiley-Interscience, 2007. If both nitrogen and hydroxyl protecting groups are present, these are preferably selected to be removable by the same conditions.

If this deprotection is carried out in a solvent of formula HQR$^Q$, then $R^{10}$ and $R^{11}$ will be H and QR$^Q$ respectively. Alternatively, these groups may be introduced by adding the compound to a different solvent to that in which the deprotection is carried out.

The conversion of compounds of formula I as discussed above to those having $R^{11}$ as $SO_xM$ may be achieved by the addition of the appropriate bisulphite salt or sulphinate slat, followed by a purification step. Further methods are described in GB 2 053 894, which is herein incorporated by reference.

Compounds of formula 2 can be made by the coupling of compounds of Formula 3 and Formula 4:

(3)

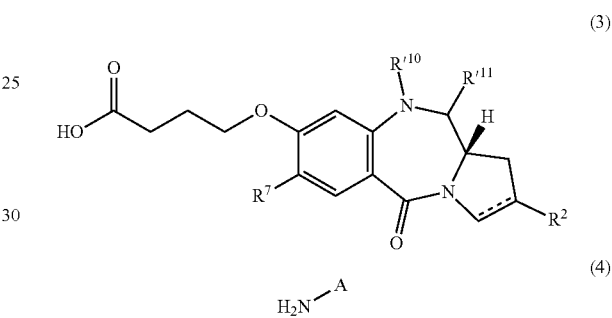

(4)

$H_2N$—A under standard amide bond formation conditions, e.g. in the presence of HOBt or DMAP and EDCI.

Compounds of formula 3 can be synthesised from compounds of formula 5:

(5)

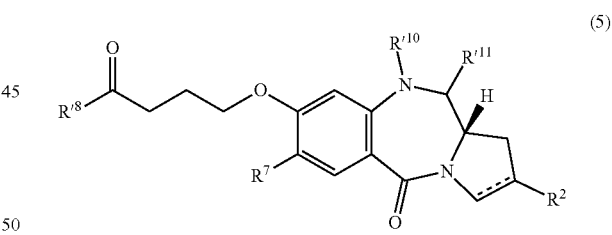

where $R'^8$ is a $C_{1-4}$ alkyl group, e.g. methyl. This deprotection of the carboxyl group may be carried out using standard means, e.g. treatment with base.

Compounds of formula 5 can be synthesised in general following the methods described in WO 00/12506 and WO 2007/039752, which are herein incorporated by reference. In particular, the butanoic acid side chain can be introduced at any stage in the synthesis, usually with appropriate protecting groups in place. For example, the side chain can be formed by coupling a protected or precursor form to a hydroxy group on the bezene ring using e.g. Mitsunobo coupling.

Compounds of formula 4 can be synthesised using the methods disclosed in WO 2005/085177, which are incorporated herein by reference. Reference is also made to the disclosure of WO 2007/039752.

DNA Binding

The ability of the compounds to bind to DNA, and in particular oligonucleotides, can be measured using an Ion Pair Reversed-Phase HPLC assay, as described in Rahman, K. M., et al., *Journal of the American Chemical Society* 2009, 131, 13756 and Narayanaswamy, M., et al., *Analytical Biochemistry* 2008, 374, 173. The DNA binding affinity can also be evaluated by using a calf-thymus DNA thermal denaturation assay, as described in Wells, G., et al., *Journal of Medicinal Chemistry* 2006, 49, 5442; Jenkins, T. C., et al., *Journal of Medicinal Chemistry* 1994, 37, 4529; and Gregson, S. J., et al., *Journal of Medicinal Chemistry* 2001, 44, 737.

Further Preferences

C2

It may be preferred in any of the embodiments that the C2 carbon is a $sp^2$ centre, so that when $R^2$ is selected from any of the following groups:
—H, —OH, —CN, —R, —OR, halo, —O—$SO_2$—R, —$CO_2R$ and —COR
there is a double bond between C2 and C3.

When $R^2$ is selected from any of the following groups:
=O, =$CH_2$, =CHR, =CHRR'
there cannot be a double bond between C2 and C3.

$R^2$ $R^2$ is selected from —H, —OH, =O, =$CH_2$, —CN, —R, OR, halo, dihalo, =CHR, =CHRR', —O—$SO_2$—R, $CO_2R$ and COR.

In some embodiments, $R^2$ may be selected from —H, —OH, =O, =$CH_2$, —CN, —R, —OR, =CHR, =CRR', —O—$SO_2$—R, —$CO_2R$ and —COR.

In some embodiments, $R^2$ may be selected from —H, =$CH_2$, —R, =CHR, and =CRR'.

In one embodiment, $R^2$ is H.
In one embodiment, $R^2$ is =O.
In one embodiment, $R^2$ is =$CH_2$.
In one embodiment, $R^2$ is =CHR. Within the PBD compound, the group =CHR may have either configuration shown below:

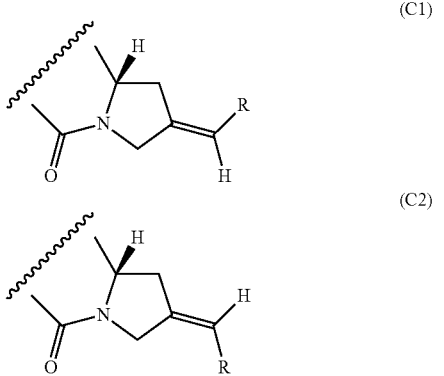

In one embodiment, the configuration is configuration (C1).

In one embodiment, $R^2$ is =CRR'.
In one embodiment, $R^2$ is =$CF_2$.
In one embodiment, $R^2$ is R.
In one embodiment, $R^2$ is optionally substituted $C_{5-20}$ aryl.
When $R^2$ is optionally substituted $C_{5-20}$ aryl, it may preferably be optionally substituted $C_{5-7}$ aryl or $C_{8-10}$ aryl. $R^2$ may further preferably be optionally substituted phenyl, optionally substituted napthyl, optionally substituted pyridyl, optionally substituted quinolinyl or isoquinolinyl. Of these groups, optionally substituted phenyl is most preferred.

When $R^2$ is optionally substituted $C_{5-20}$ aryl, it may preferably bear one to three substituent groups, with 1 and 2 being more preferred, and singly substituted groups being most preferred. The substituents may be any position.

Where $R^2$ is a $C_{5-7}$ aryl group, a single substituent is preferably on a ring atom that is not adjacent the bond to the remainder of the compound, i.e. it is preferably P or y to the bond to the remainder of the compound. Therefore, where the $C_{5-7}$ aryl group is phenyl, the substituent is preferably in the meta- or para-positions, and more preferably is in the para-position.

In one embodiment, $R^2$ is selected from:

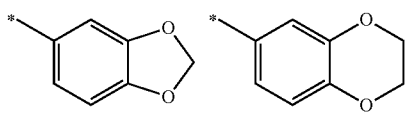

where the asterisk indicates the point of attachment.

Where $R^2$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

When $R^2$ is optionally substituted $C_{5-20}$ aryl, the substituents may be selected from: halo, hydroxyl, ether, formyl, acyl, carboxy, ester, acyloxy, amino, amido, acylamido, aminocarbonyloxy, ureido, nitro, cyano and thioether.

When $R^2$ is optionally substituted $C_{5-20}$ aryl, the substituents may be selected from the group consisting of R, OR, SR, NRR', $NO_2$, halo, $CO_2R$, COR, $CONH_2$, CONHR, and CONRR'.

If a substituent on $R^2$ is halo, it is preferably F or Cl, more preferably Cl.

If a substituent on $R^2$ is ether, it may in some embodiments be an alkoxy group, for example, a $C_{1-7}$ alkoxy group (e.g. methoxy, ethoxy) or it may in some embodiments be a $C_{5-7}$ aryloxy group (e.g phenoxy, pyridyloxy, furanyloxy).

If a substituent on $R^2$ is $C_{1-7}$ alkyl, it may preferably be a $C_{1-4}$ alkyl group (e.g. methyl, ethyl, propyl, butyl).

If a substituent on $R^2$ is $C_{3-7}$ heterocyclyl, it may in some embodiments be $C_6$ nitrogen containing heterocyclyl group, e.g. morpholino, thiomorpholino, piperidinyl, piperazinyl.

These groups may be bound to the rest of the PBD moiety via the nitrogen atom. These groups may be further substituted, for example, by $C_{1-4}$ alkyl groups.

If a substituent on $R^2$ is bis-oxy-$C_{1-3}$ alkylene, this is preferably bis-oxy-methylene or bis-oxy-ethylene.

Particularly preferred substituents for $R^2$ include methoxy, ethoxy, fluoro, chloro, cyano, bis-oxy-methylene, methyl-piperazinyl, morpholino and methyl-thienyl.

Particularly preferred substituted $R^2$ groups include, but are not limited to, 4-methoxy-phenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthienyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl.

In one embodiment, $R^2$ is optionally substituted $C_{1-12}$ alkyl.

When $R^2$ is optionally substituted $C_{1-12}$ alkyl, it may be selected from:

(a) $C_{1-5}$ saturated aliphatic alkyl;
(b) $C_{3-6}$ saturated cycloalkyl;
(c)

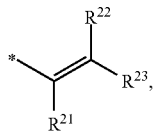

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;
(d)

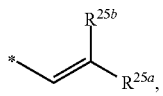

wherein one of $R^{25a}$ and $R^{25b}$ is H and the other is selected from: phenyl, which phenyl is optionally substituted by a group selected from halo methyl, methoxy; pyridyl; and thiophenyl; and
(e)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^{12}$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^{12}$ is $C_{3-6}$ saturated cycloalkyl, it may be cyclopropyl, cyclobutyl, cyclopentyl or cyclohexyl. In some embodiments, it may be cyclopropyl.

When $R^{12}$ is

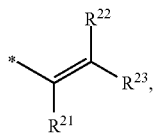

each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5. In some embodiments, the total number of carbon atoms in the $R^{12}$ group is no more than 4 or no more than 3.

In some embodiments, one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that are not H are methyl.

In some embodiments, $R^{21}$ is H.
In some embodiments, $R^{22}$ is H.
In some embodiments, $R^{23}$ is H.
In some embodiments, $R^{21}$ and $R^{22}$ are H.
In some embodiments, $R^{21}$ and $R^{23}$ are H.
In some embodiments, $R^{22}$ and $R^{23}$ are H.
When $R^{12}$ is

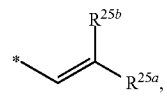

one of $R^{25a}$ and $R^{25b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^{12}$ is

$R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted. In some embodiments, $R^{24}$ is selected from H, methyl, ethyl, ethenyl and ethynyl. In some of these embodiments, $R^{24}$ is selected from H and methyl.

In one embodiment, $R^2$ is halo or dihalo. In one embodiment, $R^2$ is —F or —$F_2$, which substituents are illustrated below as (C3) and (C4) respectively:

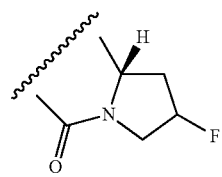
(C3)

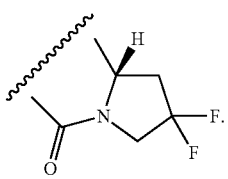
(C4)

$R^2$ may preferably selected from =$CH_2$, =CH—R, where R is more preferably an optionally substituted $C_{1-4}$ alkyl group, and —R, where R is more preferably an optionally substituted C$_{5-20}$ aryl group. Particularly preferred groups for R$^2$ include =CH$_2$, =CH-Me, and an optionally substituted phenyl group.

R$^7$

R$^7$ is selected from H, R, OH, OR, SH, SR, NH$_2$, NHR, NRR', nitro, Me$_3$Sn and halo;

R$^7$ may preferably be selected from H, OR, SH, SR, NH$_2$, NHR, NRR', and halo.

R$^7$ may more preferably be selected from H and OR.

In some embodiments, R$^7$ is OR, and more particularly OR$^{7A}$, where R$^{7A}$ is independently optionally substituted C$_{1-7}$ alkyl.

R$^{7A}$ may be selected from optionally substituted saturated C$_{1-7}$ alkyl and optionally substituted C$_{2-4}$ alkenyl.

R$^{7A}$ may preferably be selected from Me, CH$_2$Ph and allyl.

R$^{10}$/R$^{11}$

R$^{10}$ and R$^{11}$ either together form a double bond, or are selected from H and QR$^Q$ respectively, where Q is selected from O, S and NH and R$^Q$ is H or C$_{1-7}$ alkyl or H and SO$_x$M, where x is 2 or 3, and M is a monovalent pharmaceutically acceptable cation;

In some embodiments, R$^{10}$ and R$^{11}$ form a double bond together.

In some embodiments, R$^{10}$ is H and R$^{11}$ is OR$^Q$. In these embodiments, R$^Q$ may preferably be selected from H or Me.

In some embodiments, R$^{10}$ is H and R$^{11}$ is SO$_x$M. x may preferably be 3, and M may preferably be Na$^+$.

R$^1$

R$^1$ is C$_{1-4}$ alkyl.

R$^1$ may preferably be C$_{1-2}$ alkyl, and more preferably methyl.

A

A is selected from A1, A2, A3, A4 or A5.

X$^1$ and Y$^1$

For each of A1, A2, A3, A4 and A5, X$^1$ and Y$^1$ are selected from: CH and NH; CH and NMe; N and NMe; CH and S; N and S; N and O; and CH and O, respectively.

Preferably X$^1$ and Y$^1$ are selected from: CH and NMe; N and NMe; CH and S; and CH and O, respectively. Most preferably, X$^1$ and Y$^1$ are selected from N and NMe and CH and NMe, respectively.

F

F is selected from a single bond and -(E-F$^1$)$_m$—.

When F is -(E-F$^1$)$_m$—, each E is independently selected from a single bond, and —C(=O)—NH—; each F$^1$ is independently a C$_{3-20}$ heteroarylene group; and m is 1, 2 or 3.

Preferably, F$^1$ is a C$_{5-6}$ heteroarylene group, more preferably a C$_5$ heteroarylene group. More preferably, F$^1$ is represented by structure F11:

(F11)

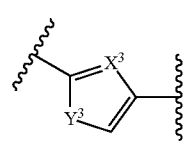

wherein X$^3$ and Y$^3$ are selected from: CH and NH; CH and NMe; N and NMe; CH and S; N and S; N and O; and CH and O, respectively. Preferably X$^3$ and Y$^3$ are selected from: CH and O; and CH and NMe, respectively.

Thus, preferred structures of F11 are:

| X$^3$ | Y$^3$ | F11 |
|---|---|---|
| CH | NMe | 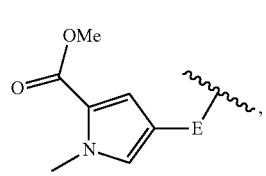 |
| CH | O | 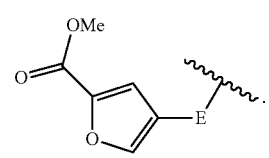 |

Each E is independently selected from a single bond and —C(=O)—NH—. In some embodiments, each E is —C(=O)—NH—.

m is 1, 2 or 3. Preferably m is 1. In other embodiments, m is 3.

In some embodiments F is a single bond.

G

G is selected from hydrogen, C$_{1-4}$alkyl, —C(=O)—O—C$_{1-4}$alkyl, —(CH$_2$)$_n$—C$_{3-20}$ heterocycloalkyl, and —O—(CH$_2$)$_n$—C$_{3-20}$ heterocycloalkyl group; and each n is 0-4.

Preferably, the C$_{3-20}$ heterocycloalkyl group is a morphiline group. Preferably, G is selected from the group consisting of —H, -Me, —C(=O)—O-Me, —(CH$_2$)$_n$—N(CH$_2$CH$_2$OCH$_2$CH$_2$), and —O—(CH$_2$)$_n$—N(CH$_2$CH$_2$OCH$_2$CH$_2$).

n is 0-4. Thus, n may be 0, 1, 2, 3 or 4.

Preferred Combinations of F and G

In some embodiments, G and at least one of the (-E-F$^1$)— units of F are provided by the structures FG1 and FG2:

(FG1)

(FG2)

FG1 and FG2 may be combined with other -(E-F$^1$)— units of F if m is 2 or 3.

A1

A1 is represented by the structure:

(A1)

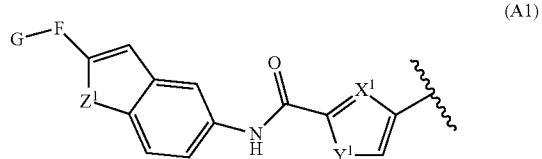

Z$^1$ is O or S. Preferably X$^1$ and Y$^1$ are selected from CH and NMe, and N and NMe.

Thus preferred structures of A1 are A11, A12, A13 and A14:

| X¹ | Y¹ | Z¹ | A1 |
|---|---|---|---|
| CH | NMe | O | 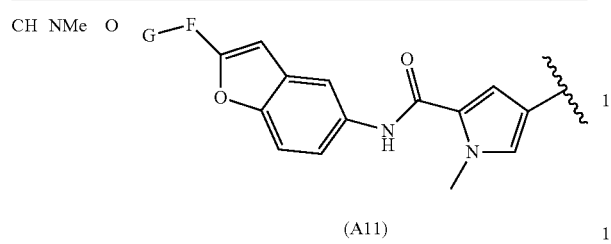 (A11) |
| N | NMe | O | 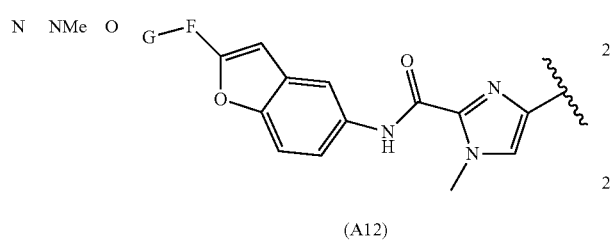 (A12) |
| CH | NMe | S | 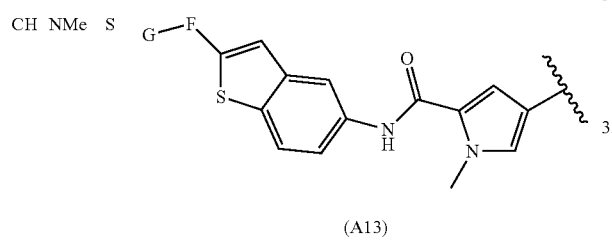 (A13) |
| N | NMe | S | 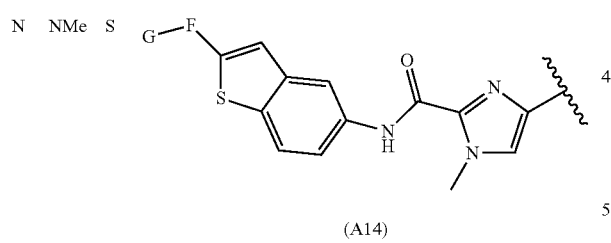 (A14) |

A2

A2 is represented by the structure:

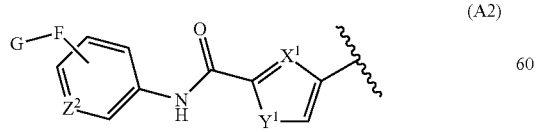

(A2)

Preferably X¹ and Y¹ are selected from CH and NMe, and N and NMe. Thus, preferred structures of A2 are A21, A22, A23 and A24:

| X¹ | Y¹ | Z² | A2 |
|---|---|---|---|
| CH | NMe | CH | 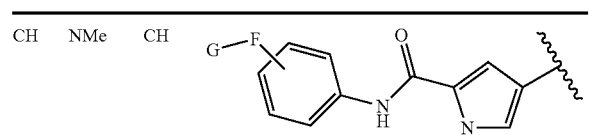 (A21) |
| N | NMe | N | 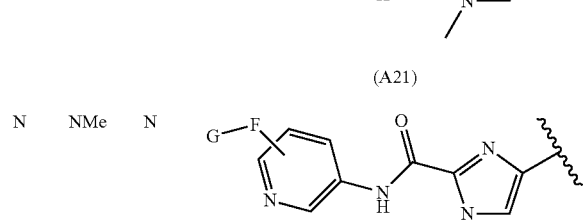 (A22) |
| N | NMe | CH | 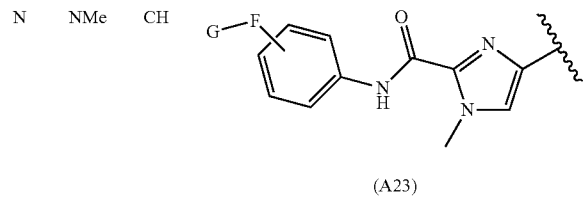 (A23) |
| CH | NMe | N | 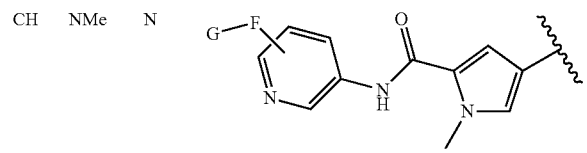 (A24) |

Preferably —F-G is arranged in the para-position of the phenylene or pyridinyl group of A2.

When A2 is represented by structures A21 or A23, A may not be A2':

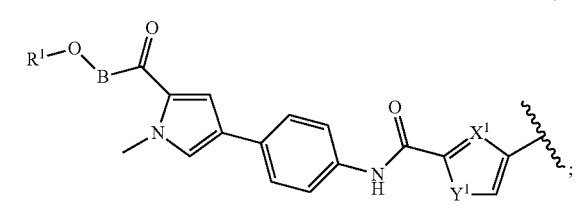

(A2')

where X¹ and Y¹ of A2' are selected from: CH and NMe and N and NMe, respectively; B is either a single bond or:

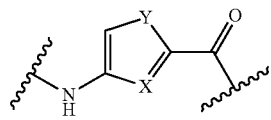

(B1)

where X and Y of (B1) are selected from: CH and NMe; COH and NMe; CH and S; N and NMe; N and S, respectively; and R¹ is $C_{1-4}$ alkyl.

A3

A3 is represented by the structure:

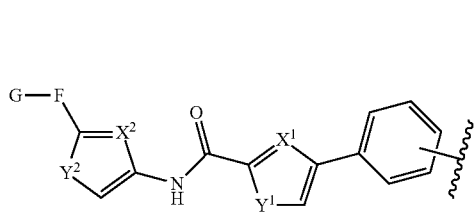
(A3)

Preferably, $X^1$ and $Y^1$ are selected from CH and NMe, N and NMe, and CH and O. Preferably $X^2$ and $Y^2$ are selected from CH and NMe, and N and NMe.

Thus preferred structures of A3 are A31, A32, A33, A34, A35 and A36:

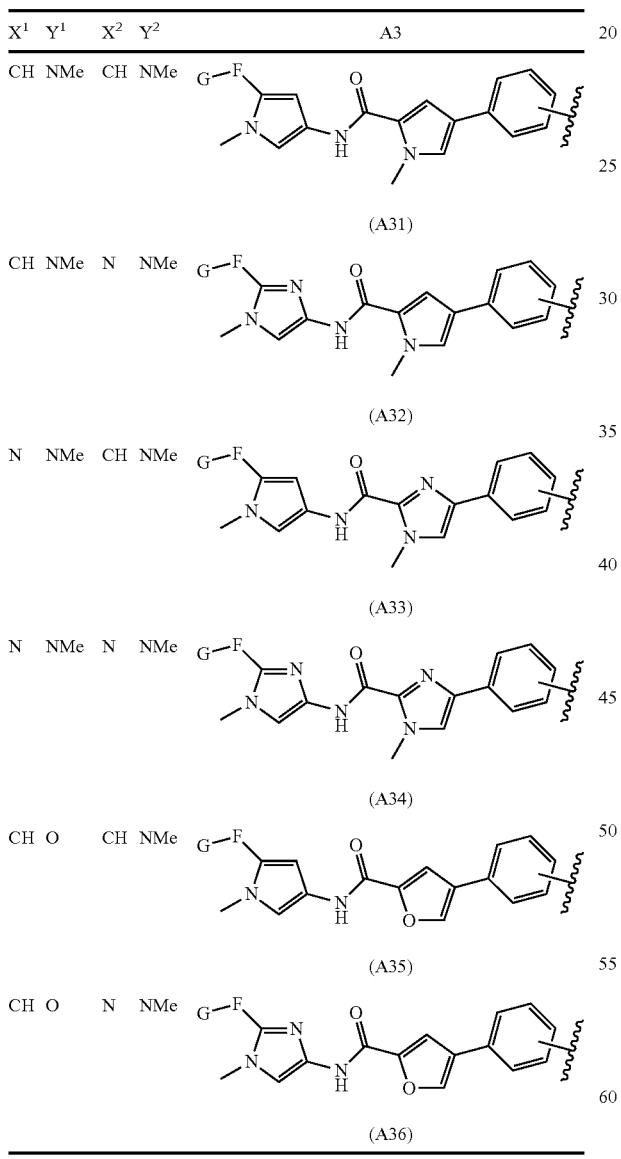

| $X^1$ | $Y^1$ | $X^2$ | $Y^2$ | A3 |
|---|---|---|---|---|
| CH | NMe | CH | NMe | (A31) |
| CH | NMe | N | NMe | (A32) |
| N | NMe | CH | NMe | (A33) |
| N | NMe | N | NMe | (A34) |
| CH | O | CH | NMe | (A35) |
| CH | O | N | NMe | (A36) |

Preferably the PBD portion of the compound is arranged in the para-position of the phenylene group of A3.

When A3 is represented by structures A31 or A32, A may not be A3':

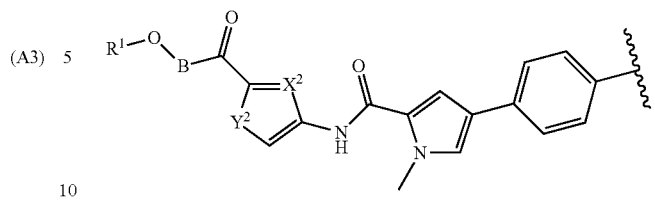
(A3')

where $X^2$ and $Y^2$ of A3' are selected from: CH and NMe; COH and NMe; CH and S; N and NMe; N and S, respectively;

B is either a single bond or:

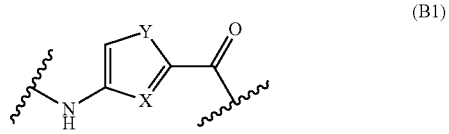
(B1)

where X and Y of B1 are selected from: CH and NMe; COH and NMe; CH and S; N and NMe; N and S, respectively; and $R^1$ is $C_{1-4}$ alkyl.

A4

A4 is represented by the structure:

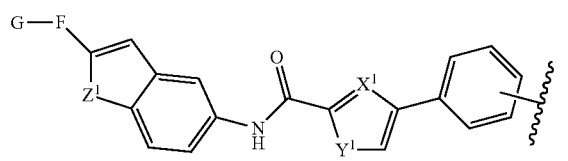
(A4)

Preferably, $X^1$ and $Y^1$ are CH and O and $Z^1$ is NMe. Thus a preferred structure of A4 is A41:

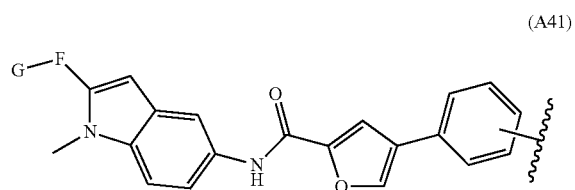
(A41)

A5

A5 is represented by the structure

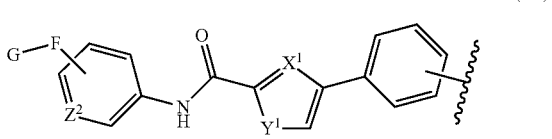
(A5)

Preferably $X^1$ and $Y^1$ are selected from CH and NMe, and CH and O. So preferred structures of A5 are given as A51, A52, A53 and A54:

| X[1] | Y[1] | Z[2] | A5 |
|---|---|---|---|
| CH | NMe | CH | 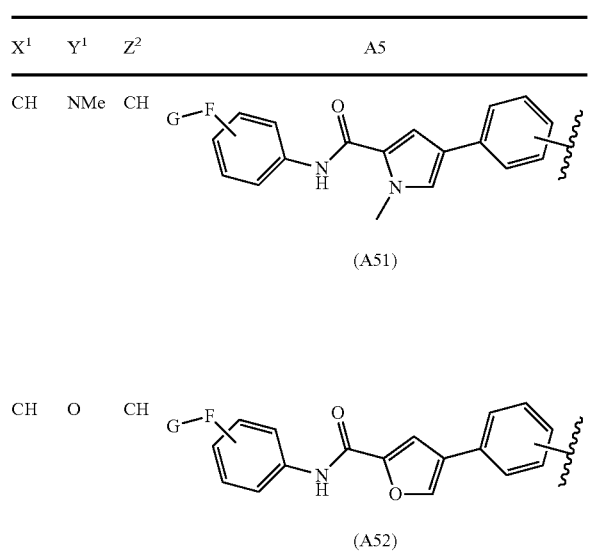 (A51) |
| CH | O | CH | (A52) |
| X[1] | Y[1] | Z[2] | A5 |
|---|---|---|---|
| CH | NMe | N | 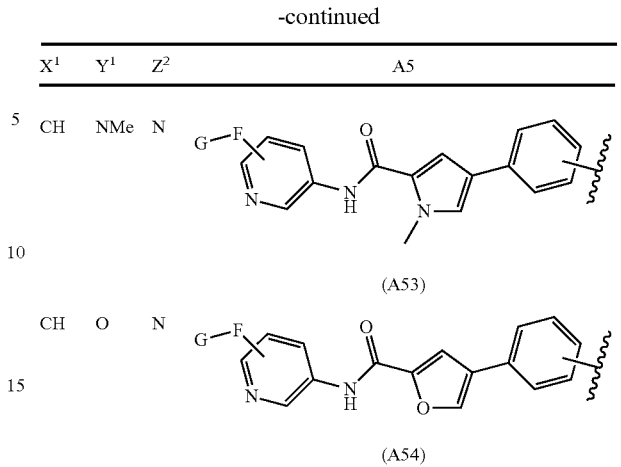 (A53) |
| CH | O | N | (A54) |
When $Z^2$ of A5 is CH, F is preferably a single bond.
Preferred compounds of the present invention are as follows:
26
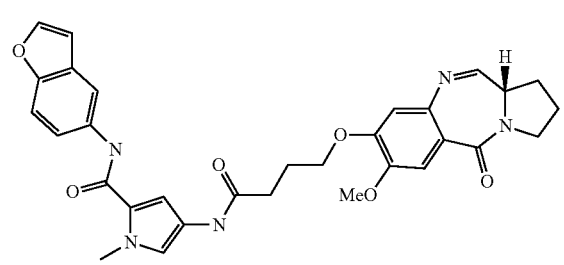
27
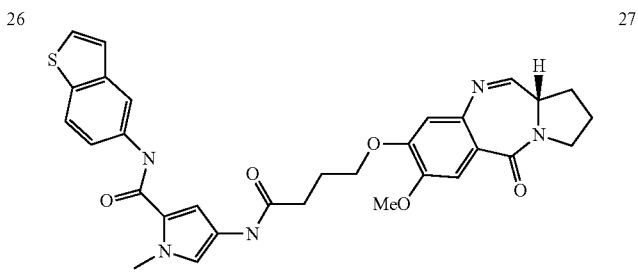
28
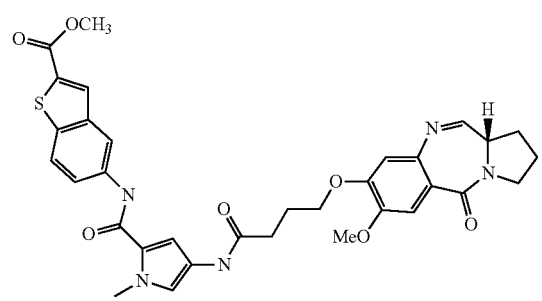
30
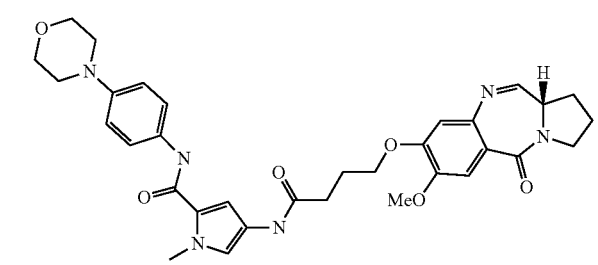
31
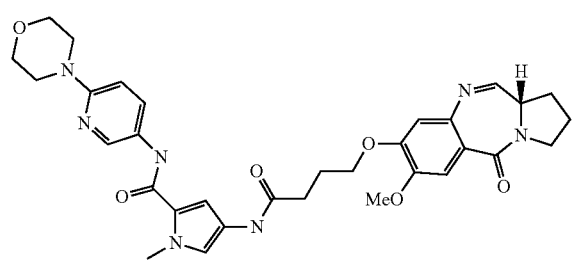
33
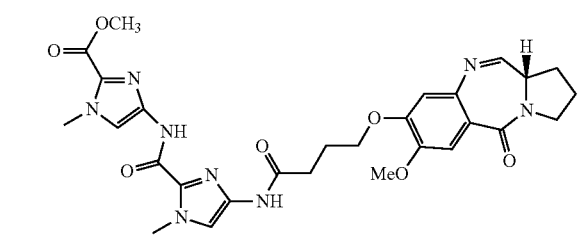

35
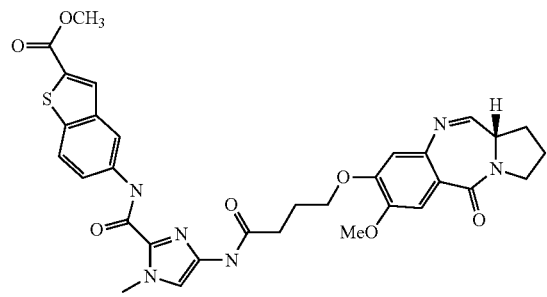
37
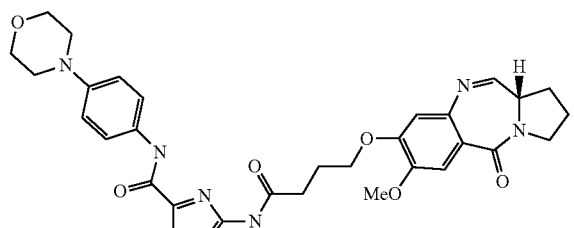
39
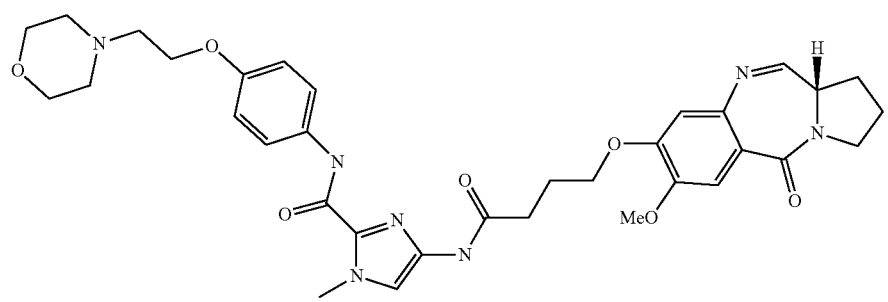
40
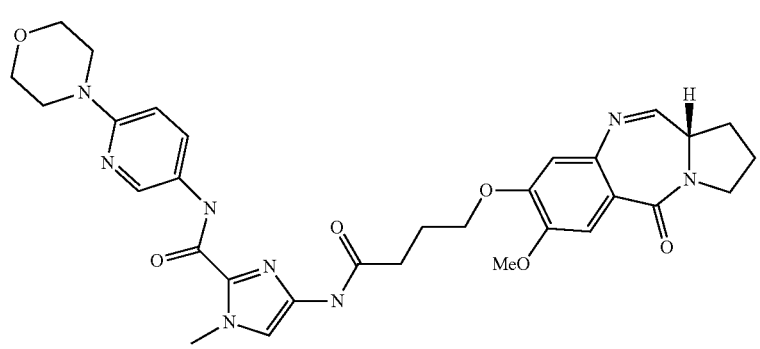
49
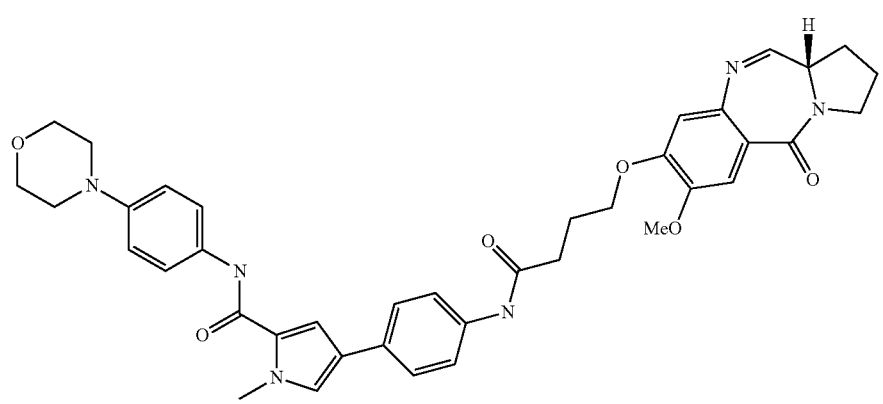

-continued
51
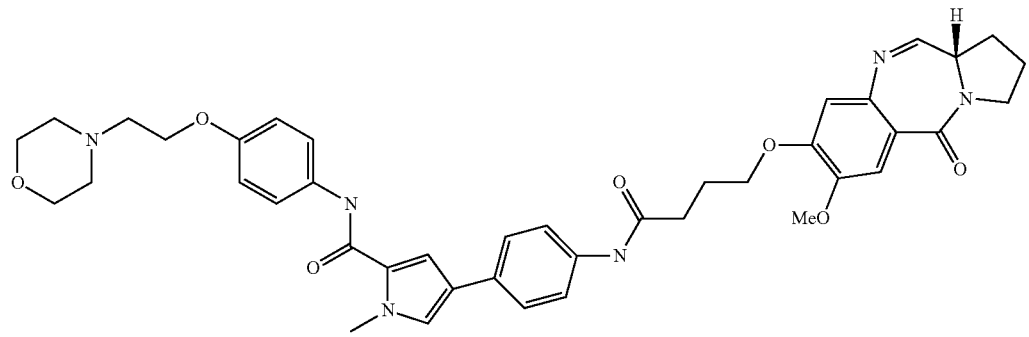
52
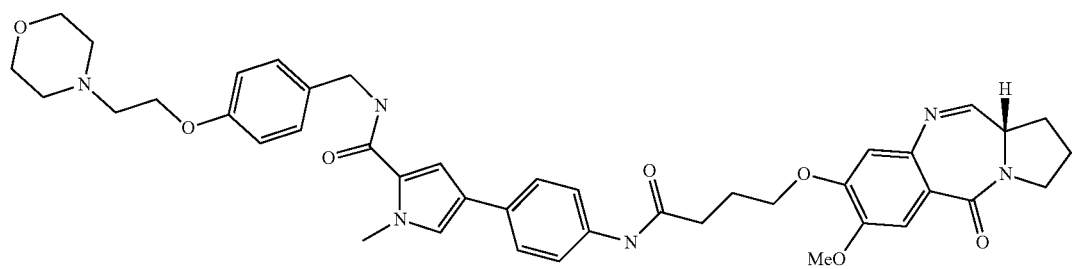
53
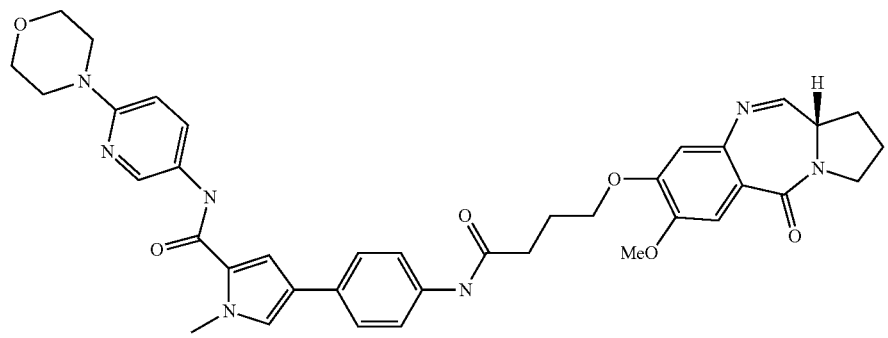
54
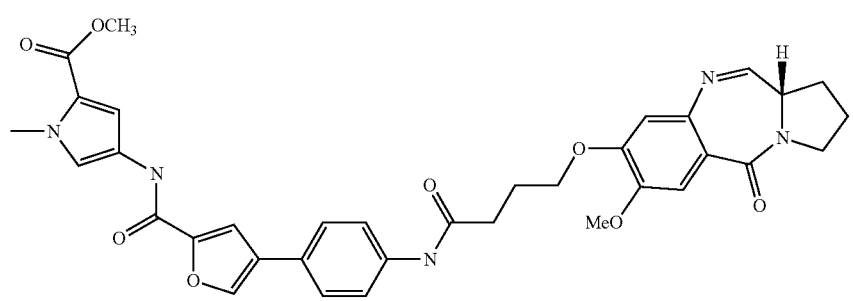
56
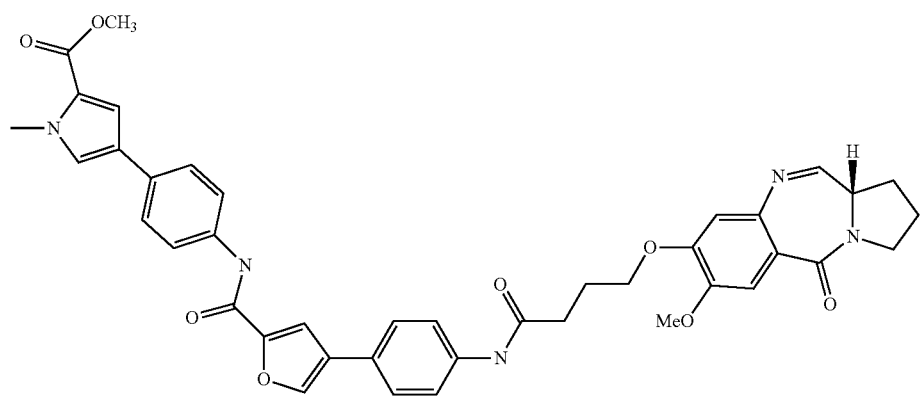

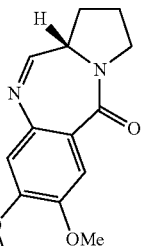
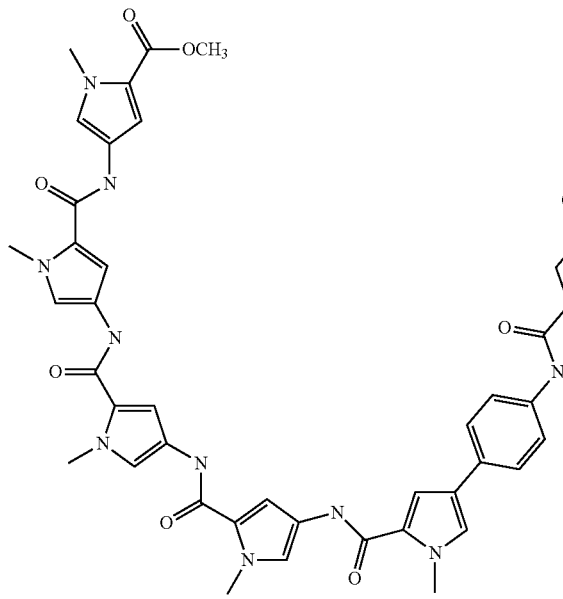

Compounds 26, 27, 28, 35, 54, and 56 are preferred. Compounds 26, 27, and 35 are more preferred, and compound 35 is particularly preferred.

EXAMPLES

General Methods

Optical rotations were measured on an ADP 220 polarimeter (Bellingham Stanley Ltd) and concentrations (c) are given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Advance NMR spectrometer at 400 and 100 MHz, respectively. Chemical shifts are reported relative to TMS ($\delta$=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). A pro-PBD numbering system is used for carbon and proton assignments for synthetic intermediates (i.e., based on the final tricyclic PBD ring system). Mass spectrometry data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; Desolvation flow rate (L/h), 250. High-resolution mass spectrometry data were recorded on a Waters Micromass QTOF Global in positive W-mode using metal-coated borosilicate glass tips to introduce the samples into the instrument. Thin Layer Chromatography (TLC) was performed on silica gel aluminum plates (Merck 60, F$_{254}$), and flash chromatography utilized silica gel (Merck 60, 230-400 mesh ASTM). Parallel reactions were carried out using a Radleys™ Green House Synthesizer and parallel purifications were carried out using an IST Vacmaster™. For reactions carried out in parallel, solvents were evaporated using a Genevac VC 2000D (Genevac Technologies, UK). Purified compounds were freeze dried using a Heto-Lyolab 3000 freeze drier. Hydrogenation reactions were carried out using UHP-60H hydrogen generator attached to a Parr hydrogenation apparatus. Synthetic building blocks were purchased from Maybridge Chemicals (UK), Bachem Chemicals (USA) and Sigma-Aldrich (UK). Reagents and solvents were purchased from Sigma-Aldrich (UK).

Synthesis of Intermediates (a) Methyl 4-(4-(tert-butoxycarbonylamino)phenyl)-1-methyl-1H-pyrrole-2-carboxylate (5)

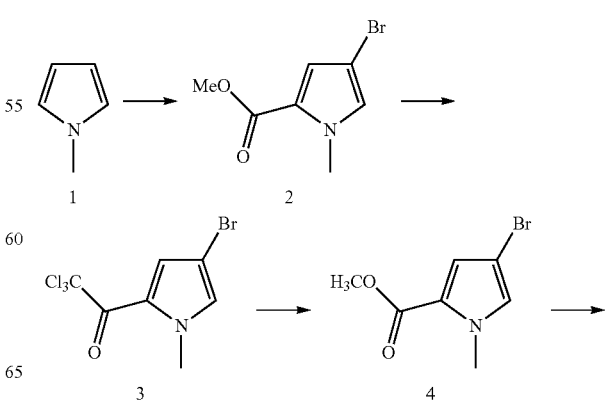

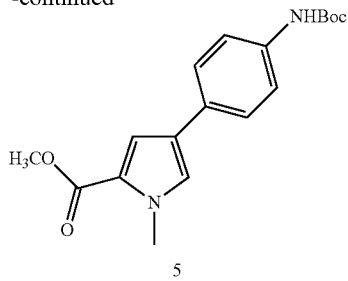

(i) 2-(trichloroacetyl)-1-methyl pyrrole (2)

A solution of N-methyl pyrrole (1)(113.06 g, 1.39 mol, 1.0 eq) in dry ether (350 mL) was added drop wise over a period of 1 hour and 10 minutes to a stirred solution of trichloroacetyl chloride (254 g, 1.39 mol, 1.0 eq) in dry ether (350 mL) in a 2 L, 3 necked flask. HCl gas produced in the reaction was removed by flushing with nitrogen. The reaction mixture was allowed to stir for 1.5 hours and progress of the reaction was monitored regularly by TLC and LCMS. After 1.5 hours the reaction was quenched using 1 M $K_2CO_3$ solution. The reaction mixture was extracted with ethyl acetate (3×) and the organic layers were combined and concentrated in vacuo. The crystalline residue was washed with n-hexane and finally dried under vacuum. Yield—281.18 g, 79.5%, NMR compared with literature IR, (FTIR, $v_{max}/cm^{-1}$) 3299, 3121, 3008, 2954, 1789, 1674, 1521, 1406, 1206, 1100, 980, 881, 757; $^1$H-NMR (CDCl$_3$, 400 MHz) δ 7.42 (1H, dd, J=4.4, 1.6 Hz), 6.97 (1H, t, J=1.6 Hz), 6.22 (1H, dd, J=4.4, 2.4 Hz) 3.97 (3H, s); $^{13}$C NMR (CDCl$_3$, 400 MHz): δ 133.6, 124.0, 122.4, 108.9, 38.5.

(ii) 1-(4-bromo-1-methyl-1H-pyrrol-2-yl)-2,2,2-trichloroethanone (3)

NBS (N-Bromosuccinimide, 2.36 g, 13.24 mmol, 1.0 equiv.) was added to a stirred solution of 2-(trichloroacetyl)-1-methylpyrrole (2) (3 g, 13.24 mmol, 1.0 equiv.) in anhydrous THF (35 mL) at −10° C. The reaction mixture was kept at −10° C. for 2 hours and then left to reach room temperature (ca. 4 hours). Excess THF was evaporated in vacuum and the solid was re-dissolved in a mixture of EtOAc/n-hexane (1:9). The resulting mixture was filtered through a plug of silica, and the filtrate was evaporated in vacuo. The resulting solid was recrystallised from n-hexane to give 3 (3.55 g, 88%). IR (FTIR, $v_{max}/cm^{-1}$): 3148, 2956, 1669 (C=O), 1458, 1215, 1189, 1062, 923, 842, 823, 748, 678; $^1$H-NMR (CDCl$_3$, 400 MHz) δ 7.46 (1H, d, J=2.0 Hz), 6.95 (1H, d, J=1.6 Hz) 3.95 (3H, s); $^{13}$C NMR (CDCl$_3$, 100 MHz): δ 172.4, 132.8, 124.6, 132.2, 96.1, 38.7; EIMS m/z (+EI) calc. for C$_7$H$_5$BrCl$_3$NO (M)$^+$ 305.38, LCMS analysis found 306.86 (M+H)$^+$ (iii) Methyl 4-bromo-1-methyl-1H-pyrrole-2-carboxylate (4)

To a stirred solution of 1-(4-bromo-1-methyl-1H-pyrrol-2-yl)-2,2,2-trichloro-ethanone (3) (3.28 g, 10.74 mmol, 1 eq.) in dry MeOH (30 mL), a solution of sodium methoxide (0.5 mL) was added by a syringe. The sodium methoxide solution was prepared from NaH 60% in mineral oil (43 mg, 1.07 mmol, 0.1 eq.), which was previously washed with n-hexane. The solution was heated to reflux over a period of 30 minutes, when the TLC analysis showed complete consumption of the starting material. A few drops of concentrated H$_2$SO$_4$ were added to the solution to neutralise the base (pH 2). The excess MeOH was evaporated in vacuum and the resulting oil was redissolved in EtOAc (50 mL) and washed with water (40 mL). The aqueous layer was extracted with EtOAc (3×40 mL), and the organic phases were combined, dried (MgSO$_4$), filtered and concentrated in vacuum to afford the product as a pale white solid. (2.28 g, 97%). IR (FTIR, $v_{max}/cm^{-1}$): 3138, 2948, 1692, 1472, 1334, 1245, 1115, 1082, 921, 823, 753; $^1$H-NMR (400 MHz, CDCl$_3$): δ 6.89 (d, 1H, J=2.0 Hz), 6.76 (d, 1H, J=2.0 Hz), 3.89 (s, 3H), 3.81 (s, 3H); $^{13}$C-NMR (100 MHz, CDCl$_3$): δ 160.8, 128.7, 122.9, 119.2, 95.1, 51.2, 36.9; EIMS m/z (+EI) calc. for C$_7$H$_8$BrNO$_2$ (M)$^+$ 218.05. found 219.26 (M+H)$^+$ (iv) Methyl 4-(4-(tert-butoxycarbonylamino)phenyl)-1-methyl-1H-pyrrole-2-carboxylate (5)

A catalytic amount of tetrakis(triphenylphosphine)palladium, Pd(PPh$_3$)$_4$ (0.477 g, 0.413, 0.06 eq) was added to a solution of 4 (1.5 g, 6.88 mmol, 1 eq) and (4-((tert-butoxycarbonyl)amino)phenyl)boronic acid (1.57 g, 6.88 mmol, 1.20 eq) in a 9:3:1 combination (13.5 ml) of EtOH, toluene and water in the presence of K$_2$CO$_3$ (2.856 g, 3 eq.) in a 10-20 mL microwave vial containing a magnetic stirrer. The reaction vessel was flushed with nitrogen during each addition. The reaction mixture was sealed in an inert N$_2$ atmosphere and heated with microwave radiation in an EMRYS™ Optimizer Microwave Station (Personal Chemistry) at 100° C. for 12 minutes. After LCMS and TLC analysis revealed completion of the reaction, the cooled reaction mixture was diluted with water (50 mL), extracted with EtOAc (3×40 mL), the filtrates combined, dried over MgSO$_4$ and concentrated under vacuum. The resulting oil was subjected to flash chromatography (n-hexane/EtOAc 9:1) to give 5 (Yield—2.2 g, 97%). IR (FTIR, $v^{max}/cm^{-1}$): 3353, 2975, 1696, 1521, 1441, 1366, 1264, 1235, 1209, 1058, 822, 799, 657; $^1$H-NMR (400 MHz, CDCl$_3$): δ 7.40 (d, 2H, J=8.8 Hz), 7.33 (d, 2H, J=8.8 Hz), 7.16 (d, 1H, J=2.0 Hz), 7.02 (d, 1H, J=2.0), 6.45 (br s, 1H), 3.95 (s, 3H), 3.83 (s, 3H), 1.52 (s, 9H); $^{13}$C-NMR (100 MHz, CDCl$_3$): δ 161.7, 152.8, 136.5, 129.5, 125.9, 125.6, 123.7, 123.0, 119.0, 114.6, 80.5, 51.1, 36.9, 28.4; EIMS m/z (+EI) calc. for C$_{18}$H$_{22}$N$_2$O$_4$ (M)$^+$ 330.38. found 330.46 (M+H)$^+$ (b) 4-(4-(tert-butoxycarbonylamino)phenyl)-1-methyl-1H-pyrrole-2-carboxylic acid (6)

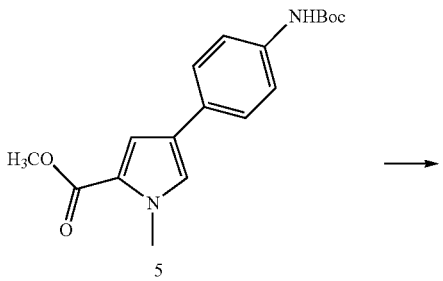

-continued

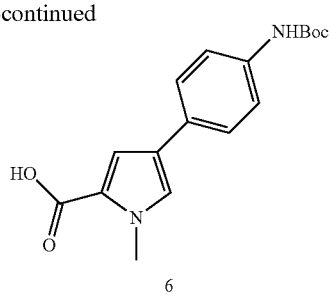

6

A 0.5 M solution of NaOH (2.0 eq) was added to a solution of 5 (1.0 g, 3.027 mmol) in dioxane (40 mL). The reaction mixture was allowed to stir at room temperature for 6 hours at which point TLC revealed completion of reaction. Excess 1,4-dioxane was evaporated under vacuum and the residue was diluted with water. The resulting solution was acidified with 0.5 M HCl. The product was extracted from water with 2× ethyl acetate (100 mL×2) and the organic layers were combined, washed with brine, dried over MgSO$_4$ and concentrated in vacuo. The product was purified using flash chromatography (ethyl acetate/n-hexane 2:8). Yield—0.92 g, 96.8%. IR (FTIR, v$^{max}$/cm$^{-1}$): 3371, 2979, 1698, 1671, 1522, 1445, 1367, 1285, 1161, 1112, 1047, 823, 803, 762, 714, 631; $^1$H-NMR (400 MHz, CDCl$_3$): δ 8.33 (1H, s), 7.55 (d, 2H, J=8.8 Hz), 7.50 (d, 2H, J=8.8 Hz), 7.36 (d, 1H, J=2.0 Hz), 7.22 (d, 1H, J=2.0), 3.97 (s, 3H), 1.50 (s, 9H); $^{13}$C-NMR (100 MHz, CDCl$_3$): δ 162.3, 153.7, 138.6, 123.0, 127.1, 126.0, 124.4, 124.0, 119.5, 115.1, 79.9, 36.9, 28.6; EIMS m/z (+EI) calc. for C$_{17}$H$_{20}$N$_2$O$_4$ (M)$^+$ 316.35. found 315.16 (M+H)$^+$ (c)

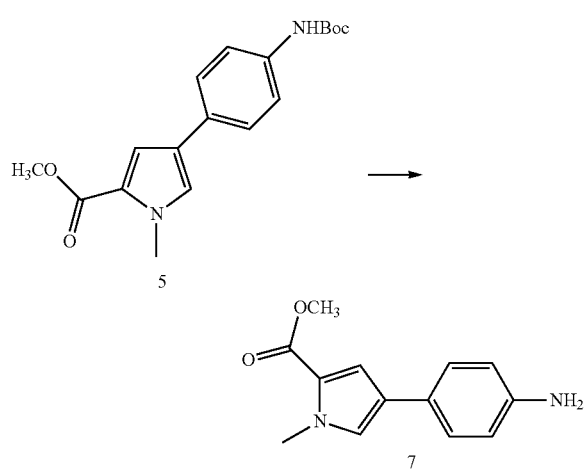

(i) Methyl 4-(4-aminophenyl)-1-methyl-1H-pyrrole-2-carboxylate (7)

5 (1 g, 3.027 mmol) was dissolved in a small volume of MeOH and 4M HCl in dioxane (15 mL) was added slowly to the stirring solution. The reaction mixture was stirred for 6 hours at which point TLC showed completion of reaction. Excess solvent was evaporated under vacuum to obtain a brown coloured solid 7. The solid product was subjected to flash chromatography (n-hexane/EtOAc 9:1) to give pure 7 (065 g, 94.2%). IR (FTIR, v$^{max}$/cm$^{-1}$): 3366, 2987, 1688, 1629, 1566, 1422, 1372, 1262, 1181, 1103, 1067, 951, 821, 784, 756; $^1$H-NMR (400 MHz, CDCl$_3$): δ 7.28 (2H, d, J=8.4 Hz), 7.11 (1H, d, J=2.0 Hz), 6.96 (1H, d, J=2.0 Hz), 6.68 (d, 2H, J=8.0 Hz), 3.94 (s, 3H), 3.83 (s, 3H); $^{13}$C-NMR (100 MHz, CDCl$_3$): δ 161.7, 144.7, 126.2, 125.4, 125.2, 115.5, 114.4, 51.0, 36.8; EIMS m/z (+EI) calc. for C$_{13}$H$_{14}$N$_2$O$_2$ (M)$^+$ 230.26. found 231.1 (M+H)$^+$ (d)

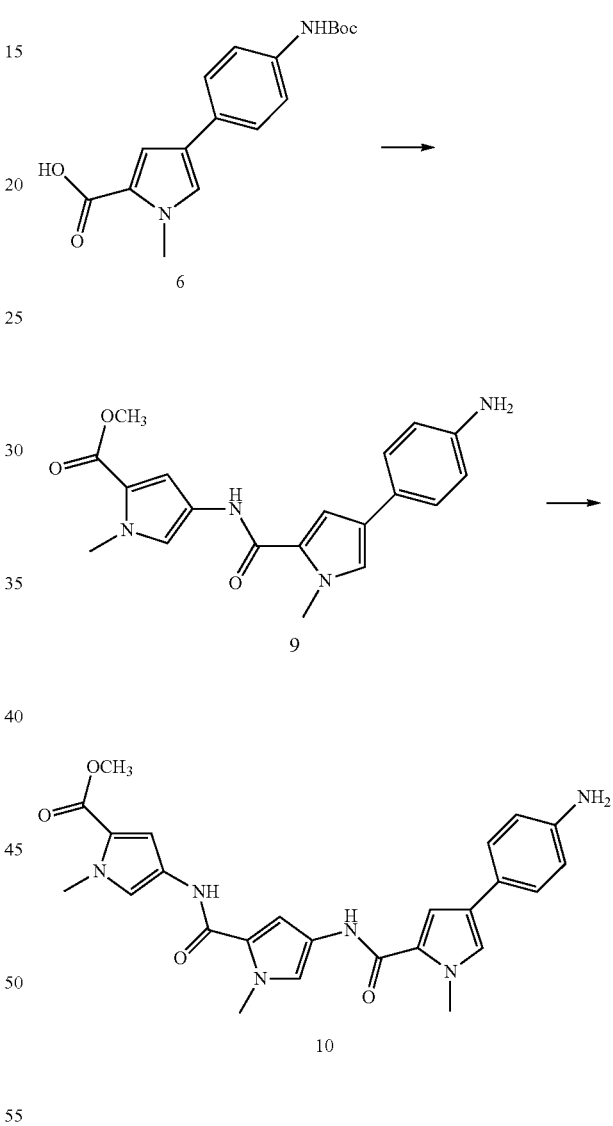

(i) Methyl 4-(4-(4-aminophenyl)-1-methyl-1H-pyrrole-2-carboxamido)-1-methyl-1H-pyrrole-2-carboxylate (9)

Two eq of EDCI and 2.5 eq of DMAP were added to a stirred solution of 6 (0.45 gm, 1.2 eq) in DMF (8 mL) and the mixture was allowed to stir for 30 minutes after which commercially available methyl 4-amino-1-methyl-1H-pyrrole-2-carboxylate (0.18 g, 1.18 mmol, 1.0 eq) was added. The reaction mixture was allowed to stir for a further 6 hour at which point TLC showed completion of reaction. The reaction was quenched by pouring it onto a mixture of ice/water mixture and the resulting mixture was extracted with ethyl acetate (3×150 mL). The combined extracts were sequentially washed with citric acid (100 mL), saturated aqueous NaHCO₃ (100 mL), water (100 mL), brine (100 mL) and finally dried over MgSO₄. Excess ethyl acetate was evaporated by rotary evaporator under reduced pressure and the crude product 9a (0.58 gm, yield 90.6%) was used for the boc deprotection step to afford 9 without further purification. For boc deprotection, 0.29 gm of 9a was dissolved in a small volume of MeOH and 4M HCl in dioxane (15 mL) was added slowly to the stirring solution. The reaction mixture was stirred for 6 hours at which point TLC showed completion of reaction. Excess solvent was evaporated under vacuum to obtain a brown coloured solid (9). The solid product was subjected to flash chromatography (n-hexane/EtOAc 9:1) to give pure 9. Yield 0.21 gm, 95%.

(ii) Methyl 4-(4-(4-(4-aminophenyl)-1-methyl-1H-pyrrole-2-carboxamido)-1-methyl-1H-pyrrole-2-carboxamido)-1-methyl-1H-pyrrole-2-carboxylate (10)

Lithium hydroxide (68 mg, 1.65 mmol, 3 eq) was added to 9a (0.25 g, 0.55 mmol) in aqueous dioxane (8 ml dioxane, 4 ml water) at room temperature. The reaction mixture was stirred for 3 hours at which point TLC showed completion of reaction. Dioxane was evaporated under high vacuum and the residue was diluted with water. The resulting solution was acidified with 1 M citric acid followed by extraction with ethyl acetate (2×50 mL). The organic layer combined and washed with brine (50 mL), dried over MgSO₄ and finally concentrated using a rotary evaporator under reduced pressure to obtain the hydrolysed acid from of 9a as a white solid (yield 0.23 g, 91.6%). To a stirring solution of the white solid (0.23 gm, 0.52 nmol) in DMF, 2.0 equivalent of EDCI and 2.5 Equivalent of DMAP was added. After stirring the mixture for 20 minutes, commercially available methyl 4-amino-1-methyl-1H-pyrrole-2-carboxylate (80.1 mg, 0.52 mmol, 1.0 eq) was added. The reaction mixture was allowed to stir for a further 3 hour at which point TLC showed completion of reaction. The reaction was quenched by pouring it onto a mixture of ice/water mixture and the resulting mixture was extracted with ethyl acetate (3×50 mL). The combined extracts were sequentially washed with saturated aqueous NaHCO₃ (50 mL) and brine (50 mL) and finally dried over MgSO₄. Excess ethyl acetate was evaporated by rotary evaporator under reduced pressure and the crude product was used for the boc deprotection step to afford 10. For boc deprotection, the crude intermediate was dissolved in a small volume of MeOH and 4M HCl in dioxane (5 mL) was added slowly to the stirring solution. The reaction mixture was stirred for 3 hours at which point TLC showed completion of reaction. Excess solvent was evaporated under vacuum to obtain a brown coloured solid (10). The solid product was subjected to flash chromatography (n-hexane/EtOAc 8:2) to give pure 10. Yield 0.20 gm, 83% over 2 steps. ¹H-NMR (DMSO, 400 MHz): δ 9.72 (1H, s), 8.09 (1H, t, J=5.6 Hz), 7.71 (2H, d, J=8.8 Hz), 7.49 (2H, d, J=8.8 Hz), 7.40 (1H, d, J=2.0 Hz), 7.27 (1H, d, J=2.0), 7.19 (1H, d, J=2.0), 7.03 (1H, dd, J=4.0, 1.6 Hz), 7.00 (1H, t, J=2.0 Hz), 6.84 (1H, d, J=2.0 Hz), 6.10 (1H, m), 3.89 (3H, s). m/z (+EI) calc. for C₂₅H₂₆N₆O₄ (M)⁺ 474.51. found 475.35 ([M+H]⁺

(e)

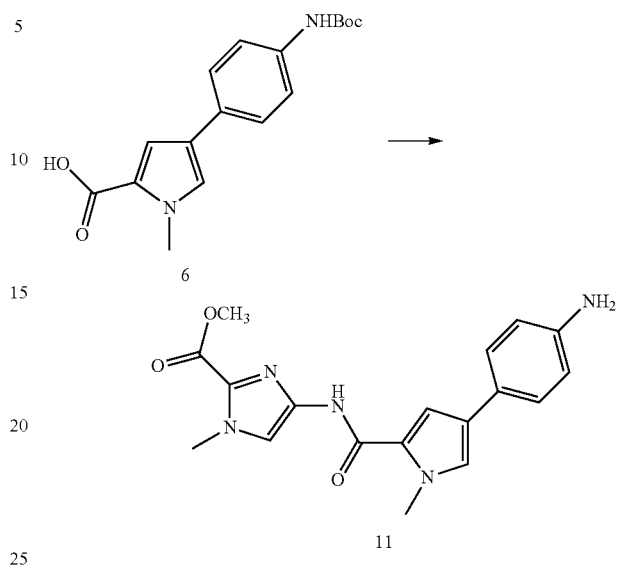

Methyl 4-(4-(4-aminophenyl)-1-methyl-1H-pyrrole-2-carboxamido)-1-methyl-1H-imidazole-2-carboxylate (11)

0.3 gm of boc protected 6 (0.94 mmol, 1.2 eq) was dissolved in DMF (5 mL) to which 2.0 eq of EDCI and 2.5 eq of DMAP were added. The mixture was allowed to stir for 30 minutes after which commercially available methyl 4-amino-1-methyl-1H-imidazole-2-carboxylate (0.121 g, 0.79 mmol, 1.0 eq) was added. The reaction mixture was allowed to stir for a further 6 hour at which point TLC showed completion of reaction. The reaction was quenched by pouring it onto a mixture of ice/water mixture and the resulting mixture was extracted with ethyl acetate (3×150 mL). The combined extracts were sequentially washed saturated aqueous NaHCO₃ (50 mL), water (50 mL), brine (50 mL) and finally dried over MgSO₄. Excess ethyl acetate was evaporated by rotary evaporator under reduced pressure and the crude product (0.48 gm) was used for the boc deprotection step to afford 11. For boc deprotection, the crude intermediate was dissolved in a small volume of MeOH and 4M HCl in dioxane (5 mL) was added slowly to the stirring solution. The reaction mixture was stirred for 2 hours at which point TLC showed completion of reaction. Excess solvent was evaporated under vacuum to obtain a brown coloured solid (11). The solid product was subjected to flash chromatography (n-hexane/EtOAc 9:1) to give pure 11. Yield 0.35 gm, 81% over two steps.

¹H-NMR (DMSO, 400 MHz): 9.75 (1H, s), 8.03 (1H, s), 7.71 (2H, d, J=8.8 Hz, 7.53 (1H, s), 7.52 (1H, s), 7.48 (2H, d, J=8.8 Hz), 7.42 (1H, s), 7.19 (1H, d, J=2.0), 3.94 (3H, s), 3.91 (3H, s), 3.89 (3H, s). m/z (+EI) calc. for C₁₈H₁₉N₅O₃ (M)⁺ 353.38. found 354.42 ([M+H]⁺

(f) 4-(10-(allyloxycarbonyl)-7-methoxy-5-oxo-11-(tetrahydro-2H-pyran-2-yloxy)-2,3,5,10,11,11a-hexahydro-1H-pyrrolo[2,1-c][1,4]benzodiazepine-8-yloxy)butanoic acid (13)

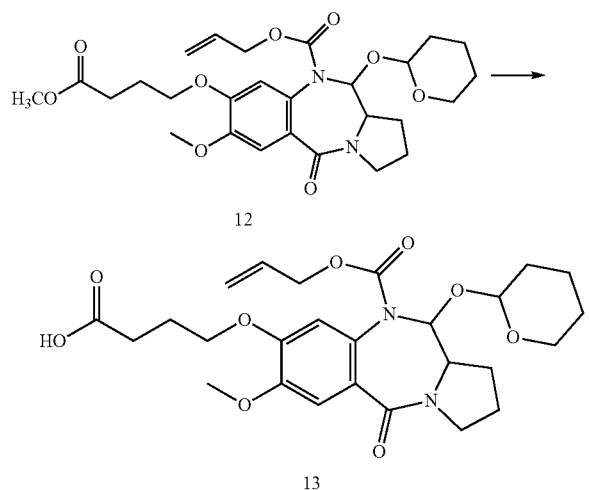

A 0.5 M solution of NaOH (made from 1.4135 g of NaOH) was added to a solution of 12 (Compound 18, WO 2007/039752) in dioxane at room temperature. The reaction mixture was allowed to stir for 4 hours at which point TLC showed completion of the reaction. Dioxane was evaporated under high vacuum and the residue was diluted with water. The resulting solution was acidified with 1 M citric acid followed by extraction with ethyl acetate (2×100 mL). The combined organic layers were washed with brine (100 mL), dried over MgSO$_4$ and finally concentrated using a rotary evaporator under reduced pressure. Yield—8.7 g, (94%), $^1$H-NMR (400 MHz, CDCl3): δ 7.2 (2H, s), 6.90 (1H, s), 6.58 (1H, s), 5.85 (2H, d, J=9.2 Hz), 5.73 (2H, d, J=9.2 Hz), 5.03-5.13 (m, 6H), 4.68-4.35 (m, 4H), 4.09-4.01 (m, 4H), 3.91-3.82 (m, 8H), 3.69-3.46 (m, 8H), 2.60-2.55 (m, 4H), 2.18-2.00 (m, 10H), 1.76-1.55 (m, 4H), 1.53-1.43 (m, 8H); $^{13}$C-NMR (100 MHz, CDCl3): δ 177.6, 167.6, 149.8, 132.1, 131.9, 126.7, 117.3, 114.9, 110.8, 100.7, 96.0, 91.7, 88.5, 67.9, 66.6, 63.6, 60.1, 56.1, 46.5, 31.1, 30.3, 28.8, 25.2, 24.1, 23.2, 20.0; EIMS m/z (+EI) calc. for C$_{26}$H$_{34}$N$_2$O$_9$ (M)$^+$ 518.56. found 519.26 (M+H)$^+$ Other Q$^1$ and Q$^2$ amine building blocks are commercially available or synthesized analogously.

Example 1

Comparative Compounds

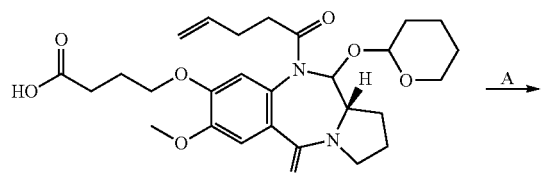

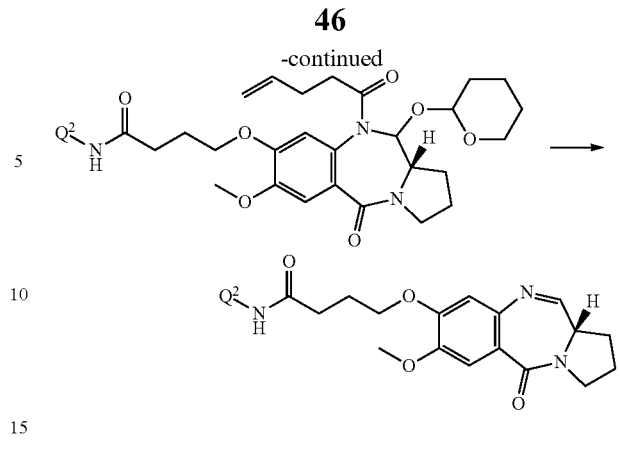

General Experimental Procedure for Coupling Different Building Blocks to Alloc-THP Protected PBD Acid to Different Building Blocks. Example Given Here is for 15a. Similar Procedures were Followed to Obtain Other C8-Linked Alloc-THP Protected PBD-Hybrids.

(11aS)-allyl 7-methoxy-8-(4-(4-(5-(methoxycarbonyl)-1-methyl-1H-pyrrol-3-yl)phenylamino)-4-oxobutoxy)-5-oxo-11-(tetrahydro-2H-pyran-2-yloxy)-2,3,11,11a-hexahydro-1H-pyrrolo[2,1-c][1,4]benzodiazepine-10(5H)-carboxylate (15a)

A solution of Alloc-THP protected PBD acid 13 (3.72 g, 7.16 mmol, 1.2 equivalent) was dissolved in DMF. EDCI (2.49 g, 13.02 mmol, 2.0 eq) and DMAP (1.989 g, 16.28 mmol, 2.5 eq) were added to the stirred solution of 13 at room temperature and the mixture was allowed to stir for 30 minutes after which the MPB-ester 7 (1.5 g, 6.514 mmol, 1.0 eq) was added. The reaction mixture was allowed to stir for a further 2 hour at which point TLC showed completion of reaction. The reaction was quenched by pouring it onto a mixture of ice/water mixture and the resulting mixture was extracted with ethyl acetate (3×150 mL). The combined extracts were sequentially washed with citric acid (200 mL), saturated aqueous NaHCO$_3$ (250 mL), water (250 mL), brine (250 mL) and finally dried over MgSO$_4$. Excess ethyl acetate was evaporated by rotary evaporator under reduced pressure and the crude product was purified by silica gel flash chromatography (MeOH: CHCl$_3$, 20:80) to give a white foamy solid, 15a. Yield—4.05 g, 85.5%.

(FTIR, v$_{max}$/cm$^{-1}$): 2949, 2362, 1704, 1600, 1514, 1436, 1372, 1269, 1203, 1107, 1021, 964, 765. ($^1$H NMR, 400 MHz, CDCl$_3$): δ 7.82 (1H, s), 7.48 (2H, m), 7.41 (1H, d, J=2.0 Hz), 7.40 (1H, d, J=2.4 Hz), 7.23 (2H, d, J=8.4 Hz), 7.17 (1H, d, J=2.0 Hz), 7.04 (1H, d, J=2.0 Hz), 5.93-5.65 (2H, m), 5.09-5.4.97 (m, 4H), 4.68-4.32 (m, 4H), 4.15-4.10 (m, 4H), 3.94-3.82 (m, 12H), 3.68 (m, 2H), 3.59-3.49 (m, 6H), 2.60-2.57 (m, 3H), 2.15-2.00 (m, 8H), 1.88-1.80 (m, 2H), 1.79-1.70 (6H), 1.60-1.44 (m, 12H); ($^{13}$C NMR, 100 MHz, CDCl$_3$): 177.1, 170.5, 167.3, 161.6, 149.1, 136.3, 132.1, 131.9, 130.4, 128.9, 127.1, 125.9, 125.4, 123.5, 123.1, 120.3, 117.3, 114.6, 110.8, 91.5, 88.6, 68.2, 66.5, 64.3, 63.6, 60.3, 56.0, 51.1, 46.4, 36.8, 31.1, 30.9, 29.1, 25.1, 24.6, 23.2, 21.0, 20.1; m/z (+EI) calc. for C$_{39}$H$_{46}$N$_4$O$_{10}$ (M)$^+$ 730.80. found 731.67 ([M+H]$^+$ General Experimental Procedure to Obtain the Final PBD Imine by Deprotecting the C8-Linked Alloc-THP Protected PBD Hybrid. Example Given Here is for 16.

Palladium tetrakis[triphenylphosphine](5.60 mg, 4.8 μM, 0.05 equiv) was added to a solution of Alloc-THP-PBD conjugate 15a (70 mg, 0.097 mmol), pyrrolidine (8.36 mg, 0.117 mmol, 1.2 eq) and triphenylphosphine (8.62 mg, 0.25 equiv) in DCM (5 mL). The reaction mixture was stirred at room temperature for 2 hours at which point TLC showed completion of reaction. Excess DCM was removed by rotary evaporation under reduced pressure and the resulting residue dried in vacuo to remove pyrrolidone. The product was purified by column chromatography (eluted with n-hexane 65%%, EtOAc 35%) to give the product as a yellowish solid, 3.37 (40 mg, 77%). $[\alpha]^{22.7}_{D}$+165° (c=0.046, CHCl3); IR (FTIR, $v^{max}$/cm$^{-1}$): 3297, 2944, 2358, 1701, 1598, 1567, 1508, 1442, 1374, 1264, 1212, 1181, 1106, 1072, 824, 730; $^1$H-NMR (500 MHz, CDCl$_3$): δ 7.68 (1H, s), 7.65 (1H, d, J=4.5 Hz, H-11), 7.52 (1H, s, H-6), 7.46 (2H, dd, J=8.4, 2.0 Hz, 2Ar—H), 7.40 (2H, dd, J=8.4, 2.0 Hz, 2Ar—H), 7.16 (1H, d, J=2.0 Hz, Py-H), 7.03 (1H, d, J=1.6 Hz, Py-H), 6.82 (1H, s, H-9), 4.12-4.20 (2H, m, CH2 side chain linker), 3.94 (3H, s, N—CH3), 3.88 (3H, s, O—CH3), 3.68-3.71 (1H, m, H-11a), 3.50-3.60 (2H, m, H2-3), 2.58-2.62 (2H, m, CH2), 2.26-2.31 (4H, m, CH2), 1.50-1.54 (2H, m, CH2); $^{13}$C-NMR (125 MHz, CDCl$_3$): δ 164.5, 162.4, 161.6, 150.5, 147.8, 140.7, 125.9, 125.5 (2C), 123.6, 123.1, 120.3, 114.6, 111.8, 111.0, 94.4 (2C), 68.0, 63.7, 56.1, 53.7, 51.0, 46.6, 36.8, 31.9, 29.6, 25.2, 24.8, 24.1, 20.2; HRMS m/z (+EI) calc. for C$_{30}$H$_{32}$N$_4$O$_6$ (M+H)$^+$ 545.2400. found 545.2422 (M+H)$^+$, δ 4 ppm Compound 18 was made in an analogous manner.

(S)-methyl 5-(4-(4-((7-methoxy-5-oxo-2,3,5,11a-tetrahydro-1H-benzo[e]pyrrolo[1,2-a][1,4]diazepin-8-yl)oxy)butanamido)phenyl)thiophene-2-carboxylate (18)

$^1$H-NMR (500 MHz, CDCl$_3$): δ 7.75 (1H, s), 7.69 (2H, d, J=8.4 Hz), 7.58 (1H, s), 7.49 (2H, d, J=8.4), 7.23 (1H, d, J=4.0 Hz), 7.13 (1H, d, J=4.0 Hz), 4.24 (2H, m, CH2 side chain linker), 3.90 (3H, s, O—CH3), 3.86 (3H, s, O—CH3), 3.71-3.73 (1H, m, H-11a), 3.50-3.60 (2H, m, H2-3), 2.55-2.67 (2H, m, CH2), 2.23-2.33 (4H, m, CH2), 1.56-1.74 (2H, m, CH2); $^{13}$C-NMR (125 MHz, CDCl$_3$): δ 164.5, 162.5, 161.4, 150.6, 147.7, 140.6, 134.5, 132.9, 132.1, 131.9, 128.6, 126.8, 120.3, 114.6, 111.8, 111.0, 94.4 (2C), 68.0, 63.7, 56.1, 53.7, 52.1, 46.6, 36.8, 31.9, 29.6, 25.2, 24.8, 24.1, 20.2; HRMS m/z (+EI) calc. for C$_{29}$H$_{29}$N$_3$O$_6$S (M+H)$^+$ 547.6200. found 547.6422 (M+H)$^+$ Example 2

Compounds of the Present Invention

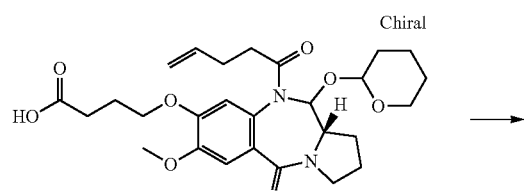

13

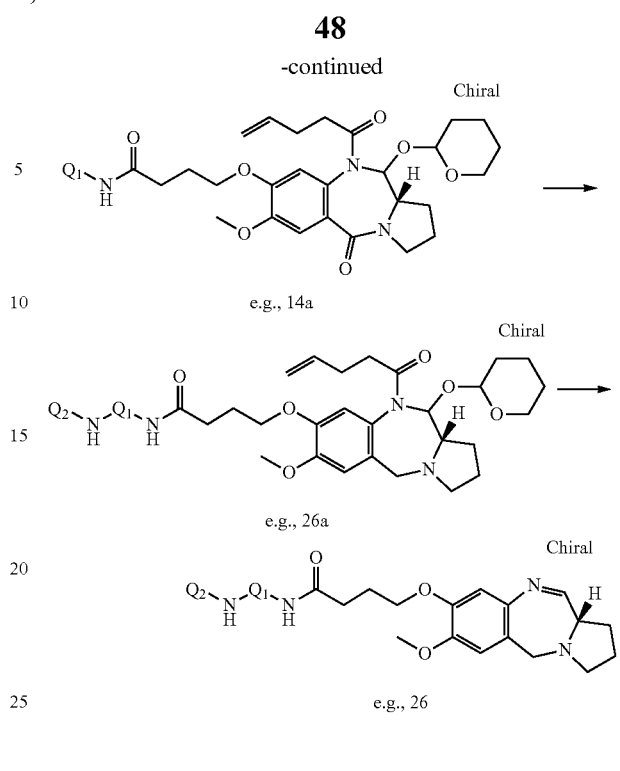

e.g., 14a e.g., 26a e.g., 26

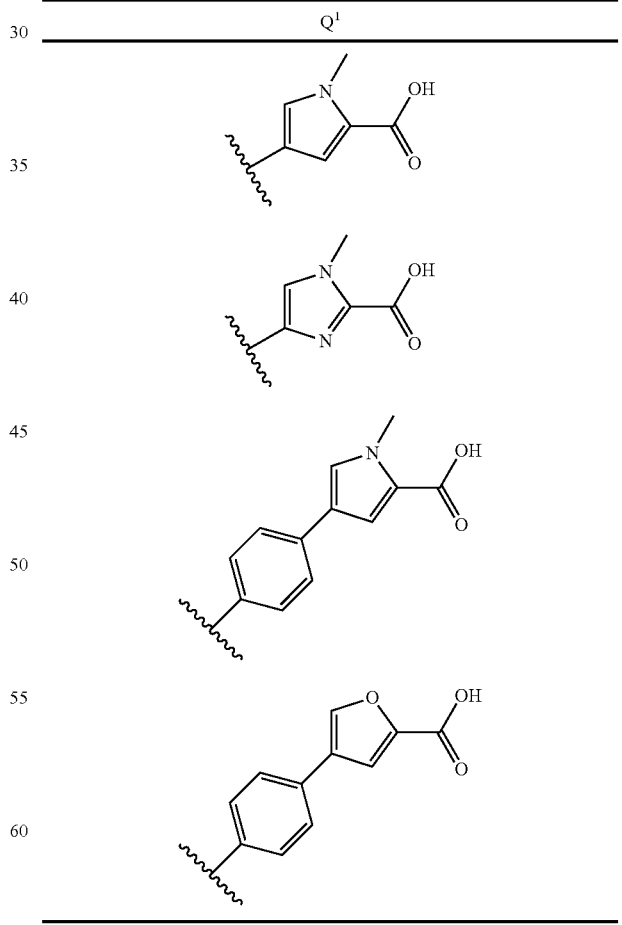

Q$^1$

General Experimental procedure for coupling different (Q1) building blocks to Alloc-THP protected PBD acid 13 to different building blocks. Example given here is for 14a.

Similar procedures were followed to obtain other C8-linked Alloc-THP protected PBD-hybrid intermediates.

(4-(((11S,11aS)-10-((allyloxy)carbonyl)-7-methoxy-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)butanamido)-1-methyl-1H-pyrrole-2-carboxylic acid (14a)

A solution of Alloc-THP protected PBD acid 13 (1.85 g, 3.57 mmol, 1.2 equivalent) was dissolved in DMF. EDCI (1.24 g, 6.48 mmol, 2.0 eq) and DMAP (0.99 g, 8.1 mmol, 2.5 eq) were added to the stirred solution of 13 at room temperature and the mixture was allowed to stir for 30 minutes after which commercially available methyl 4-amino-1-methyl-1H-pyrrole-2-carboxylate (0.5 g, 3.243 mmol, 1.0 eq) was added. The reaction mixture was allowed to stir for a further 6 hour at which point TLC showed completion of reaction. The reaction was quenched by pouring it onto a mixture of ice/water mixture and the resulting mixture was extracted with ethyl acetate (3×150 mL). The combined extracts were sequentially washed with citric acid (200 mL), saturated aqueous $NaHCO_3$ (250 mL), water (250 mL), brine (250 mL) and finally dried over $MgSO_4$. Excess ethyl acetate was evaporated by rotary evaporator under reduced pressure and the crude product (1.88 gm) was used for hydrolysis reaction to afford 14a. For hydrolysis, Lithium hydroxide (0.24 g, 5.71 mmol, 3 eq) was added to the crude product (1.88 g, 2.87 mmol) in aqueous dioxane (75 ml dioxane, 11.5 ml water) at room temperature. The reaction mixture was stirred for 3 hours at which point TLC showed completion of reaction. Dioxane was evaporated under high vacuum and the residue was diluted with water. The resulting solution was acidified with 1 M citric acid followed by extraction with ethyl acetate (2×100 mL). The organic layer combined and washed with brine (100 mL), dried over $MgSO_4$ and finally concentrated using a rotary evaporator under reduced pressure to obtain 14a as a white solid (yield, 1.68 gm, 74.0% over 2 steps).

$^1$H-NMR δ 9.09 (1H, s, NH), 7.39 (1H, d, J=2.0 Hz), 7.14 (1H, s, H-6), 7.12 (1H, s, H-6), 6.96 (1H, s, H-9), 6.76 (1H, d, J=2.0 Hz, Py-H), 5.86-5.75 (2H, m, H-11), 5.13-4.84 (3H, m), 4.61-4.21 (2H, m), 4.06-3.88 (3H, m, side-chain H-1, pyran H-6), 3.87 (3H, s, O/NCH3), 3.87 (3H, s, O/NCH3), 3.86 (3H, s), 3.53-3.44 (3H, m), 2.55-2.45 (2H, m), 2.13-1.88 (6H, m), 1.70-1.39 (6H). m/z (+EI) calc. for $C_{32}H_{40}N_4O_{10}$ (M)$^+$ 640.68. found 641.57 ([M+H]$^+$ General Experimental Procedure to Obtain 26a from 14a by Coupling Q2 Building Blocks to Q1 Building Blocks Containing Intermediates (e.g., 14a).

(11S,11aS)-allyl 7-methoxy-8-(4-((5-((4-(5-(methoxycarbonyl)-1-methyl-1H-pyrrol-3-yl)phenyl)carbamoyl)-1-methyl-1H-pyrrol-3-yl)amino)-4-oxobutoxy)-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (26a)

A solution of Alloc-THP protected PBD-Py acid 14a (150 mg, 0.23 mmol, 1.0 equivalent) was dissolved in DMF. EDCI (0.46 mmol, 2.0 eq) and DMAP (0.58 mmol, 2.5 eq) were added to the stirred solution of 14a at room temperature and the mixture was allowed to stir for 30 minutes after which the benzofuran-5-amine (38.3 mg, 0.29 mmol, 1.25 eq) was added. The reaction mixture was allowed to stir for a further 3 hour at which point TLC showed completion of reaction. The reaction was quenched by pouring it onto a mixture of ice/water mixture and the resulting mixture was extracted with ethyl acetate (3×150 mL). The combined extracts were sequentially washed with citric acid (50 mL), saturated aqueous $NaHCO_3$ (50 mL), water (50 mL), brine (50 mL) and finally dried over $MgSO_4$. Excess ethyl acetate was evaporated by rotary evaporator under reduced pressure and the crude product was directly used in the next step without further purification.

m/z (+EI) calc. for $C_{40}H_{45}N_5O_{10}$ (M)$^+$ 755.91. found 756.76 ([M+H]$^+$ Compounds 26a, 27a, 28a, 30a, 31a, 35a, 37a, 39a, 40a, 49a, 51a, 52a, 53a, 54a and 56a were obtained in an analogous manner.

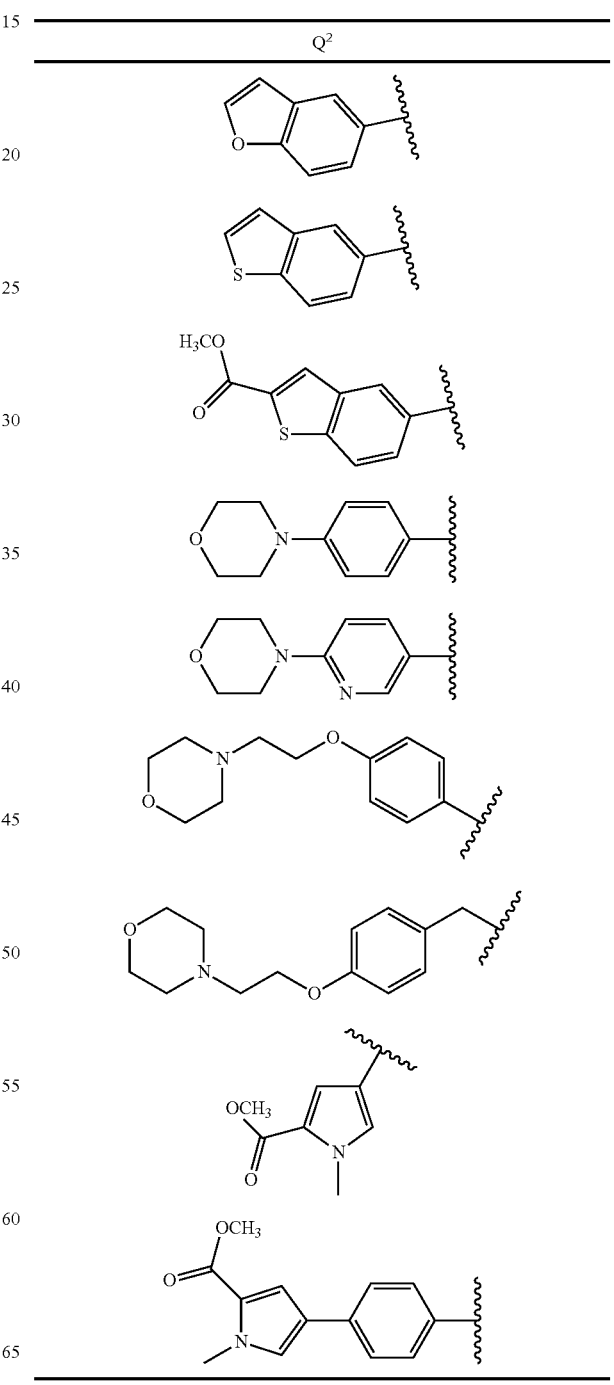

General Experimental Procedure to Obtain 26 from 26a by Simultaneous Alloc-THP Deprotection.

(i) (S)—N-(benzofuran-5-yl)-4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamide (26)

Palladium tetrakis[triphenylphosphine](12.17 mg, 10.5 µM, 0.05 equiv) was added to a solution of Alloc-THP-PBD conjugate 26a (154 mg, 0.21 mmol), pyrrolidine (17.91 mg, 0.25 mmol, 1.2 eq) and triphenylphosphine (13.81 mg, 0.25 equiv) in DCM (5 mL). The reaction mixture was stirred at room temperature for 2 h at which point TLC showed completion of reaction. Excess DCM was removed by rotary evaporation under reduced pressure and the resulting residue dried in vacuo to remove pyrrolidone. The product was purified by high performance liquid chromatography (eluted with acetone:water gradient with 1% TFA) to give the product as a light yellowish solid, 26 (38 mg, 36% after HPLC purification).

$^1$H-NMR (500 MHz, CDCl$_3$): 7.98 (1H, s), 7.94 (1H, d, J=2.0 Hz), 7.83 (1H, s), 7.65 (1H, d, J=4.4 Hz), 7.59 (1H, d, J=2.0 Hz), 7.52 (1H, s), 7.42 (1H, d, J=9.0 Hz), 7.33 (1H, dd, J=8.0 Hz, 2.0 Hz), 7.10 (1H, s), 6.82 (1H, s, H-9), 6.71 (1H, s) 4.06-4.14 (2H, m, CH$_2$), 3.90 (3H, s, N—CH$_3$), 3.88 (3H, s, O—CH$_3$), 3.66-3.72 (1H, m, H-11a), 3.50-3.59 (2H, m, H$_2$-3), 2.47-2.54 (2H, m, CH$_2$), 2.18-2.31 (4H, m, CH$_2$), 1.95-2.08 (2H, m); $^{13}$C-NMR (125 MHz, CDCl$_3$): δ 169.9, 164.6, 162.7, 159.9, 151.9, 150.6, 147.7, 145.7, 140.6, 133.2, 132.1, 128.5, 127.8, 123.4 (2C), 121.5, 120.5, 119.6, 118.0, 113.2, 111.8, 111.3, 111.0, 106.8 (2C), 103.9, 68.1, 56.2 (2C), 53.7, 46.7 (2C), 36.7 (2C), 33.1, 29.8, 24.5, 24.1; HRMS m/z (+EI) calc. for C$_{31}$H$_{31}$N$_5$O$_6$ (M)$^+$ 569.6900. found 569.6981 ([M+H]$^+$)

Compounds 27, 28, 30, 31, 35, 37, 39, 40, 49, 51, 52, 53, 54 and 56 were obtained in an analogous manner.

ii) (S)—N-(benzo[b]thiophen-5-yl)-4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamide (27)

$^1$H-NMR (500 MHz, CDCl$_3$): δ 8.23 (1H, d, J=4.5 Hz), 8.21 (1H, d, J=2.0 Hz), 7.74 (1H, d, J=8.4 Hz), 7.66 (1H, d, J=4.0 Hz), 7.61 (1H, d, J=1.6 Hz), 7.53 (1H, d, J=3.6 Hz), 7.48 (1H, s), 7.45 (2H, dd, J=8.0 Hz, 2.0 Hz), 7.39 (1H, s), 7.09 (1H, d, J=1.6 Hz), 6.80 (1H, s, H-9), 4.03-4.08 (2H, m, CH$_2$), 3.85 (3H, s, N—CH$_3$), 3.82 (3H, s, O—CH$_3$), 3.63-3.69 (1H, m, H-11a), 3.49-3.57 (2H, m, H$_2$-3), 2.44-2.49 (2H, m, CH$_2$), 2.15-2.29 (4H, m, CH$_2$), 1.95-2.04 (2H, m); $^{13}$C-NMR (125 MHz, CDCl$_3$): δ 169.9, 164.6, 162.7, 160.0, 150.7, 147.7, 140.7, 140.1, 135.1, 132.8, 131.9, 128.6, 127.3, 123.9, 123.2, 122.5, 121.6, 120.4, 119.8, 118.1, 114.8, 111.8, 110.9, 104.2, 68.1, 56.1 (2C), 53.7, 46.7 (2C), 36.7 (2C), 32.9, 29.5, 24.9, 24.2;

iii) (S)-methyl 5-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamido)benzo[b]thiophene-2-carboxylate (28)

$^1$H-NMR (500 MHz, CDCl$_3$): δ 8.29 (1H, d, J=2.0 Hz), 8.10 (1H, s), 7.97 (1H, s), 7.76 (1H, d, J=8.0 Hz), 7.73 (1H, s), 7.66 (1H, dd, J=8.0 Hz, 2.0 Hz), 7.64 (1H, d, J=1.6 Hz), 7.55 (2H, dd, J=8.0 Hz, 2.0 Hz), 7.47 (2H, d, J=3.0 Hz), 7.11 (1H, s), 6.83 (1H, s, H-9), 4.09-4.15 (2H, m, CH$_2$), 3.93 (3H, s, N—CH$_3$), 3.90 (3H, s, O—CH$_3$), 3.87 (3H, s, O—CH$_3$), 3.68-3.73 (1H, m, H-11a), 3.51-3.60 (2H, m, H$_2$-3), 2.49-2.57 (2H, m, CH$_2$), 2.19-2.34 (4H, m, CH$_2$), 1.94-2.09 (2H, m); $^{13}$C-NMR (125 MHz, CDCl$_3$): δ 169.9, 164.6, 163.2, 150.6, 147.7, 139.3, 137.66, 135.7, 134.3, 132.8, 132.1, 132.0, 131.9, 130.5, 128.6, 123.1, 122.5, 121.5, 120.9, 120.0, 116.1, 111.8, 104.2, 101.1, 68.1, 56.2 (2C), 53.7, 52.5, 46.7 (2C), 36.7 (2C), 33.1, 29.6, 25.0, 24.2;

iv) (S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(4-morpholinophenyl)-1H-pyrrole-2-carboxamide (30)

$^1$H-NMR (500 MHz, CDCl$_3$): δ 7.71 (1H, s), 7.65 (1H, d, J=4.6 Hz), 7.52 (1H, s), 7.46 (2H, d, J=8.4 Hz), 7.06 (1H, d, J=2.0 Hz), 6.87 (2H, d, J=8.4 Hz), 6.82 (1H, s), 6.55 (1H, d, J=1.6 Hz), 4.05-4.19 (2H, m, CH$_2$), 3.88 (3H, s, N—CH$_3$), 3.85 (3H, s, O—CH$_3$), 3.73-3.82 (4H, m), 3.66-3.72 (1H, m, H-11a), 3.52-3.60 (2H, m, H$_2$-3), 3.03-3.13 (4H, m), 2.50-2.56 (2H, m, CH$_2$), 2.19-2.33 (4H, m, CH$_2$), 1.97-2.07 (2H, m); $^{13}$C-NMR (125 MHz, CDCl$_3$): δ 169.9, 164.6, 162.7, 159.6, 150.6, 148.1, 147.7, 130.8, 123.5, 121.5, 120.6, 119.5, 116.4, 111.8, 111.1, 103.8, 68.1, 66.9 (2C), 56.2 (2C), 53.7, 49.8, 46.7 (2C), 36.7 (2C), 33.1, 29.6, 25.0, 24.2;

v) (S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(6-morpholinopyridin-3-yl)-1H-pyrrole-2-carboxamide (31)

$^1$H-NMR (400 MHz, CDCl$_3$): δ 8.23 (1H, s), 7.92 (1H, s), 7.89 (1H, d, J=8.4 Hz), 7.83 (1H, s), 7.65 (1H, d, J=3.6 Hz), 7.51 (1H, s), 7.08 (1H, s), 6.82 (1H, s), 6.63 (1H, d, J=8.4 Hz), 6.56 (1H, s), 4.05-4.16 (2H, m, CH$_2$), 3.91 (3H, s, N—CH$_3$), 3.85 (3H, s, O—CH$_3$), 3.74-3.82 (4H, m), 3.67-3.71 (1H, m, H-11a), 3.51-3.61 (2H, m, H$_2$-3), 3.41-3.48 (4H, m), 2.49-2.57 (2H, m, CH$_2$), 2.17-2.26 (2H, m, CH$_2$), 1.99-2.09 (2H, m); $^{13}$C-NMR (100 MHz, CDCl$_3$): δ 169.9, 164.5, 162.7, 159.9, 156.8, 150.6, 147.7, 140.6, 131.5, 126.3, 123.0, 121.5, 120.6, 119.7, 111.9, 111.1, 106.8, 104.2, 68.1, 66.7 (2C), 56.2 (2C), 53.7, 46.7, 46.1 (2C), 41.0, 36.7 (2C), 33.1, 29.6, 25.0, 24.2;

vi) (S)-methyl 5-(4-(4-((7-methoxy-5-oxo-2,3,5,11a-tetrahydro-1H-benzo[e]pyrrolo[1,2-a][1,4]diazepin-8-yl)oxy)butanamido)-1-methyl-1H-imidazole-2-carboxamido)benzo[b]thiophene-2-carboxylate (35)

$^1$H-NMR (500 MHz, CDCl$_3$): δ 9.04 (1H, s), 8.35 (1H, s), 8.04 (1H, s), 7.74 (1H, d, J=8.4 Hz), 7.66 (1H, d, J=4.0 Hz), 7.61 (1H, d, J=1.6 Hz), 7.53 (1H, d, J=3.6 Hz), 7.48 (1H, s), 7.45 (2H, dd, J=8.0 Hz, 2.0 Hz), 7.39 (1H, s), 7.09 (1H, d, J=1.6 Hz), 4.10-4.22 (2H, m, CH$_2$), 3.96 (3H, s, N—CH$_3$), 3.94 (3H, s, O—CH$_3$), 3.80 (3H, s, O—CH$_3$), 3.66-3.71 (1H, m, H-11a), 3.50-3.57 (2H, m, H$_2$-3), 2.49-2.57 (2H, m, CH$_2$), 2.21-2.34 (4H, m, CH$_2$), 1.95-2.08 (2H, m); $^{13}$C-NMR (125 MHz, CDCl$_3$): δ 169.9, 164.6, 163.2, 150.6, 147.7, 139.3, 137.66, 135.7, 134.3, 132.9, 132.1, 132.0, 131.9, 130.5, 128.5, 123.2, 122.5, 121.5, 120.1, 120.0, 115.4, 114.8, 11.6, 111.0, 100.0, 67.7, 56.1 (2C), 53.7, 52.5, 46.7 (2C), 35.8 (2C), 33.0, 29.6, 24.7, 24.1;

vii) (S)-4-(4-((7-methoxy-5-oxo-2,3,5,11a-tetrahydro-1H-benzo[e]pyrrolo[1,2-a][1,4]diazepin-8-yl)oxy)butanamido)-1-methyl-N-(4-morpholinophenyl)-1H-imidazole-2-carboxamide (37)

$^1$H-NMR (400 MHz, CDCl$_3$): δ 8.80 (1H, s), 7.98 (1H, s), 7.83 (1H, s), 7.64 (1H, d, J=4.0 Hz), 7.54 (1H, s), 7.51 (2H, d,

J=8.4 Hz), 7.40 (1H, s), 6.90 (2H, d, J=8.4 Hz), 6.82 (1H, s), 4.05-4.18 (2H, m, CH₂), 4.01 (3H, s, N—CH₃), 3.95 (3H, s, O—CH₃), 3.74-3.82 (4H, m), 3.67-3.71 (1H, m, H-11a), 3.52-3.57 (2H, m, H₂-3), 3.11-3.14 (4H, m), 2.61-2.63 (2H, m, CH₂), 2.17-2.23 (2H, m, CH₂), 2.02-2.09 (2H, m); $^{13}$C-NMR (125 MHz, CDCl₃): b 169.9, 164.5, 162.5, 156.4, 150.5, 148.3, 147.8, 140.7, 135.7, 133.9, 130.2, 120.9, 120.6, 116.3, 114.5 (2C), 111.6, 110.9, 67.8, 66.9 (2C), 56.1 (2C), 53.7, 49.7 (2C), 46.7, 35.8 (2C), 29.6, 24.8, 24.1;

viii) (S)-4-(4-((7-methoxy-5-oxo-2,3,5,11a-tetrahydro-1H-benzo[e]pyrrolo[1,2-a][1,4]diazepin-8-yl) oxy)butanamido)-1-methyl-N-(4-(2-morpholinoethoxyl)phenyl)-1H-imidazole-2-carboxamide (39)

$^1$H-NMR (400 MHz, CDCl₃): δ 8.80 (1H, s), 7.96 (1H, s), 7.83 (1H, s), 7.65 (1H, d, J=4.0 Hz), 7.54 (1H, s), 7.51 (2H, d, J=8.8 Hz), 7.41 (1H, s), 6.90 (2H, d, J=8.8 Hz), 6.83 (1H, s), 4.17-4.22 (2H, m, CH₂), 4.06-4.12 (4H, m), 4.06 (3H, s, N—CH₃), 3.95 (3H, s, O—CH₃), 3.72-3.79 (4H, m), 3.67-3.71 (1H, m, H-11a), 3.52-3.57 (2H, m, H₂-3), 2.79-2.81 (4H, m), 2.53-2.66 (6H, m, CH₂), 2.31-2.29 (2H, m, CH₂), 2.01-2.07 (2H, m); $^{13}$C-NMR (100 MHz, CDCl₃): δ 174.7, 169.5, 167.0, 162.5, 155.6, 149.4, 147.8, 147.8, 140.7, 135.7, 131.8, 130.9, 121.3, 120.6, 115.1, 111.6, 110.9, 67.8, 66.9 (2C), 66.0, 57.6, 56.1 (2C), 54.0, 53.7, 48.2 (2C), 46.7, 35.8 (2C), 33.0, 29.6, 24.8, 24.2, 24.1;

ix) (S)-4-(4-((7-methoxy-5-oxo-2,3,5,11a-tetrahydro-1H-benzo[e]pyrrolo[1,2-a][1,4]diazepin-8-yl) oxy)butanamido)-1-methyl-N-(6-morpholinopyridin-3-yl)-1H-imidazole-2-carboxamide (40)

$^1$H-NMR (400 MHz, CDCl₃): δ 8.73 (1H, s), 8.27 (1H, s), 7.98 (2H, m), 7.64 (1H, d, J=3.6 Hz), 7.53 (1H, s), 7.42 (1H, s), 6.82 (1H, s), 6.64 (1H, d, J=7.2 Hz), 4.07-4.22 (2H, m, CH₂), 4.04 (3H, s, N—CH₃), 3.93 (3H, s, O—CH₃), 3.78-3.85 (4H, m), 3.67-3.72 (1H, m, H-11a), 3.52-3.59 (2H, m, H₂-3), 3.44-3.5 (4H, m), 2.58-2.65 (2H, m, CH₂), 2.23-2.34 (2H, m, CH₂), 2.00-2.08 (2H, m); $^{13}$C-NMR (100 MHz, CDCl₃): δ 169.6, 164.5, 162.7, 159.9, 150.4, 147.8, 140.6, 139.9, 135.8, 133.6, 130.4, 125.7, 120.7, 114.6, 111.7, 110.9, 106.8, 67.8, 66.7 (3C), 56.1 (2C), 53.7, 46.7, 46.1 (2C), 35.7 (2C), 32.9, 29.6, 24.7, 24.2;

x) (S)-4-(4-((7-methoxy-5-oxo-2,3,5,11a-tetrahydro-1H-benzo[e]pyrrolo[1,2-a][1,4]diazepin-8-yl) oxy)butanamido)phenyl)-1-methyl-N-(4-morpholinophenyl)-1H-pyrrole-2-carboxamide (49)

$^1$H-NMR (400 MHz, CDCl₃): δ 7.75 (1H, s), 7.9 (1H, s), 7.64 (1H, d, J=4.0 Hz), 7.52 (1H, s), 7.46 (2H, d, J=8.0 Hz), 7.39 (2H, d, J=8.0 Hz), 7.00 (1H, s), 6.91 (1H, s), 6.90 (2H, d, J=8.0 Hz), 6.82 (1H, s), 4.08-4.14 (2H, m, CH₂), 3.98 (3H, s, N—CH₃), 3.87 (3H, s, O—CH₃), 3.74-3.82 (4H, m), 3.69-3.74 (1H, m, H-11a), 3.55-3.4 (2H, m, H₂-3), 3.11-3.13 (4H, m), 2.58-2.60 (2H, m, CH₂), 2.25-2.31 (4H, m, CH₂), 2.03-2.06 (2H, m); $^{13}$C-NMR (100 MHz, CDCl₃): δ 175.4, 169.9, 162.5, 162.7, 150.4, 148.1, 147.7, 140.7, 130.8, 125.4, 124.9, 123.2, 121.6, 120.4, 116.4, 111.7, 110.9, 109.3, 67.9, 66.9 (2C), 56.1 (2C), 53.7, 49.8, 46.7 (2C), 36.9 (2C), 34.1, 29.6, 24.8, 24.2;

xi) (S)-4-(4-((7-methoxy-5-oxo-2,3,5,11a-tetrahydro-1H-benzo[e]pyrrolo[1,2-a][1,4]diazepin-8-yl) oxy)butanamido)phenyl)-1-methyl-N-(4-(2-morpholinoethoxyl)phenyl)-1H-pyrrole-2-carboxamide (51)

$^1$H-NMR (400 MHz, CDCl₃): δ 7.77 (1H, s), 7.73 (1H, s), 7.65 (1H, d, J=4.4 Hz), 7.52 (1H, s), 7.8 (2H, d, J=8.0 Hz), 7.45 (1H, s), 7.38 (2H, d, J=8.0 Hz), 7.00 (1H, s), 6.91 (2H, d, J=8.8 Hz), 6.83 (1H, s), 4.14-4.18 (2H, m, CH₂), 4.09-4.14 (4H, m), 3.98 (3H, s, N—CH₃), 3.87 (3H, s, O—CH₃), 3.77-3.83 (1H, m, H-11a), 3.71-3.75 (4H, m), 3.52-3.57 (2H, m, H₂-3), 2.79-2.82 (2H, m), 2.53-2.64 (6H, m, CH₂), 2.25-2.31 (4H, m, CH₂), 2.01-2.07 (2H, m); $^{13}$C-NMR (100 MHz, CDCl₃): δ 174.7, 164.6, 162.2, 159.8, 155.4, 150.5, 147.7, 140.7, 135.7, 131.8, 126.6, 125.4, 125.0, 122.0, 120.4, 115.0, 111.7, 110.9, 67.9, 66.8 (2C), 66.0, 57.6, 56.1 (2C), 54.1 (2C), 53.7, 46.7, 35.9, 33.0, 29.6, 24.8, 24.2, xii) (S)-4-(4-(4-((7-methoxy-5-oxo-2,3,5,11a-tetrahydro-1H-benzo[e]pyrrolo[1,2-a][1,4]diazepin-8-yl)oxy)butanamido)phenyl)-1-methyl-N-(4-(2-morpholinoethoxyl)benzyl)-1H-pyrrole-2-carboxamide (52)

$^1$H-NMR (500 MHz, CDCl₃): δ 7.77 (1H, s), 7.68 (1H, s), 7.65 (1H, d, J=4.0 Hz), 7.51 (1H, s), 7.44 (2H, d, J=8.0 Hz), 7.35 (2H, d, J=8.0 Hz), 7.27 (1H, s), 6.96 (1H, d, J=2.0 Hz), 6.88 (2H, dd, J=7.0, 2.0 Hz), 6.82 (1H, s), 6.73 (1H, s), 4.50 (2H, d, J=5.5 Hz), 4.10-4.20 (4H, m, CH₂), 3.98 (3H, s, N—CH₃), 3.87 (3H, s, O—CH₃), 3.78-3.83 (1H, m, H-11a), 3.68-3.71 (4H, m), 3.52-3.59 (2H, m, H₂-3), 2.80-2.82 (2H, m), 2.53-2.64 (6H, m, CH₂), 2.24-2.33 (4H, m, CH₂), 2.01-2.07 (2H, m); $^{13}$C-NMR (125 MHz, CDCl₃): δ 174.7, 164.6, 161.6, 158.1, 150.4, 147.7, 140.7, 137.5, 135.7, 131.8, 129.2, 126.6, 125.4, 124.5, 120.4, 114.9 (2C), 111.7, 110.9, 108.7, 67.9, 66.8 (2C), 66.0, 57.6, 56.1 (2C), 54.1 (2C), 53.7, 46.7, 35.9, 33.0, 29.6, 24.8, 24.2, xiii) (S)-4-(4-(4-((7-methoxy-5-oxo-2,3,5,11a-tetrahydro-1H-benzo[e]pyrrolo[1,2-a][1,4]diazepin-8-yl)oxy)butanamido)phenyl)-1-methyl-N-(6-morpholinopyridin-3-yl)-1H-pyrrole-2-carboxamide (53)

$^1$H-NMR (500 MHz, CDCl₃): δ 8.25 (1H, s), 7.96 (1H, d, J=6.5 Hz), 7.90 (1H, s), 7.85 (1H, s), 7.65 (1H, d, J=4.0 Hz), 7.51 (1H, s), 7.44 (2H, d, J=8.0 Hz), 7.35 (2H, d, J=8.0 Hz), 7.00 (1H, s), 6.95 (1H, s), 6.82 (1H, s), 6.65 (1H, d, J=9.0 Hz), 4.08-4.15 (2H, m, CH₂), 3.97 (3H, s, N—CH₃), 3.84 (3H, s, O—CH₃), 3.78-3.82 (4H, m), 3.67-3.70 (2H, m, H₂-3), 3.53-3.59 (1H, m, H-11a), 3.42-3.46 (4H, m), 2.55-2.58 (2H, m, CH₂), 2.23-2.30 (4H, m, CH₂), 1.99-2.05 (2H, m); $^{13}$C-NMR (125 MHz, CDCl₃): δ 174.7, 164.6, 162.7, 159.9, 156.8, 150.4, 147.7, 140.7, 131.6, 126.2, 125.4, 125.1, 120.4, 111.7, 110.8, 109.6, 106.9, 67.9, 66.7 (3C), 56.1, 53.7, 46.7, 46.1 (2C), 41.0, 36.9 (2C), 34.0, 29.6, 24.8, 24.2;

xiv) (S)-methyl 4-(4-(4-((7-methoxy-5-oxo-2,3,5,11a-tetrahydro-1H-benzo[e]pyrrolo[1,2-a][1,4]diazepin-8-yl)oxy)butanamido)phenyl)furan-2-carboxamido)-1-methyl-1H-pyrrole-2-carboxylate (54)

$^1$H-NMR (500 MHz, CDCl₃): δ 7.98 (1H, s, NH), 7.88 (1H, s, NH), 7.68 (1H, s, H-6), 7.65 (1H, d, J=4.0 Hz, H-11), 7.64 (2H, d, J=8.0 Hz, 2Ar—H), 7.54 (1H, d, J=1.6 Hz, Py-H), 7.52 (1H, d, J=1.6 Hz, Py-H), 7.45 (1H, d, J=2.0 Hz, Py-H), 7.33 (2H, d, J=8.0 Hz, 2Ar—H), 6.97 (1H, s, Py-H), 6.89 (1H, s, H-9), 4.08-4.18 (2H, m, CH₂), 3.97 (3H, s, N—CH₃), 3.89 (3H, s, N—CH₃), 3.84 (3H, s, O—CH₃), 3.79 (3H, s, O—CH₃), 3.66-3.70 (1H, m, H-11a), 3.55-3.60 (2H, m, H₂-3), 2.56-2.61 (2H, m, CH₂), 2.23-2.32 (4H, m, CH₂), 2.00-2.05 (2H, m); $^{13}$C-NMR (125 MHz, CDCl₃): δ 162.5, 161.6, 159.1, 150.4, 147.7, 138.4, 132.8, 132.1 131.9 (2C), 128.6, 128.4 (2C), 125.4 (2C), 124.8, 123.0, 121.0, 120.4

(2C), 116.2, 114.6 (2C), 109.9, 94.2, 67.4, 63.6, 57.1, 53.7, 51.1, 46.7, 36.9, 36.7, 34.0, 29.6, 24.2;

xv) (S)-methyl 4-(4-(4-(4-(4-((7-methoxy-5-oxo-2,3,5,11a-tetrahydro-1H-benzo[e]pyrrolo[1,2-a][1,4]diazepin-8-yl)oxy)butanamido)phenyl)furan-2-carboxamido)phenyl)-1-methyl-1H-pyrrole-2-carboxylate (56)

$^1$H-NMR (500 MHz, CDCl$_3$): δ 7.72 (1H, s, NH), 7.69 (1H, s, NH), 7.66 (1H, d, J=4.0 Hz, H-11), 7.57 (2H, d, J=8.0 Hz, 2Ar—H), 7.53 (1H, s, H-6), 7.46 (4H, d, J=8.0 Hz, 4Ar—H), 7.41 (2H, d, J=8.0 Hz, 2Ar—H), 7.20 (1H, d, J=2.0 Hz, Py-H), 7.06 (1H, d, J=2.0 Hz, Py-H), 7.02 (1H, d, J=1.6 Hz, Py-H), 6.92 (1H, s, Py-H), 6.84 (1H, s, H-9), 4.12-4.20 (2H, m, CH$_2$ side chain linker), 4.00 (3H, s, N—CH$_3$), 3.96 (3H, s, N—CH$_3$), 3.88 (3H, s, O—CH$_3$), 3.84 (3H, s, O—CH$_3$), 3.70-3.73 (1H, m, H-11a), 3.55-3.61 (2H, m, H$_2$-3), 2.58-2.62 (2H, m, CH$_2$), 2.29-2.31 (2H, m, CH$_2$), 1.93-2.06 (4H, m, CH$_2$); $^{13}$C-NMR (125 MHz, CDCl$_3$): δ 164.5, 162.4, 161.7, 150.7, 147.3, 139.2, 126.0, 125.6, 125.4 (2C), 125.2 (2C), 123.0, 120.4 (2C), 114.6 (2C), 111.4, 94.6 (2C), 68.3, 63.7, 56.1, 51.6 (2C), 41.0, 36.9, 31.9, 29.6, 25.2, 24.2, 24.1, 20.2.

Example 3

Antibacterial Evaluation

The antibacterial properties of the compounds of the invention 26, 27, 28, 30, 31, 33, 35, 37, 39, 40, 49, 51, 52, 53, 54, 56 and 59 were compared with the comparative compounds 16 and 18 against a number of bacterial strains using the CLSI broth microplate assay, as described below.

Methicillin resistant *Staphylococcus aureus* (MRSA) strains EMRSA-15 and EMRSA-16 were isolated from clinical material at the Royal Free Hospital, London; MRSA strain BB568 was a gift from Brigitte Berger-Bachi, Institute of Medical Microbiology, University of Zurich, Switzerland. The community-associated MRSA isolate USA300 was purchased from the American Type Culture Collection as BAA-1556. *S. aureus* VISA strain Mu50 is a MRSA clinical isolate with vancomycin-intermediate resistance and was isolated and provided by Keiichi Hiramatsu, Juntendo University, Tokyo. ATCC 29213 is an antibiotic susceptible *S. aureus* reference strain. Vancomycin resistant enterococcal isolates *E. faecalis* VRE1 and *E. faecium* VRE10 were isolated at the Royal Free Hospital. Bacteria were grown in Mueller-Hinton (MH) broth (Oxoid) or on MH agar plates at 37° C.

MICs of antibacterial agents were determined by the CLSI broth microplate assay as previously described (Hadjivassileva T, Stapleton P D, Thurston D E et al. Interactions of pyrrolobenzodiazepine dimers and duplex DNA from methicillin-resistant *Staphylococcus aureus*. *Int J Antimicrob Agents* 2007; 290: 672-678); agents were dissolved in DMSO prior to dilution in broth. At the concentrations used, the solvent had no effect on bacterial growth. Three MIC determinations per strain were performed in duplicate for each compound tested.

| PBD No. | Minimum inhibitory concentration (MIC mg/L) | | | | | | |
|---|---|---|---|---|---|---|---|
| | EMRSA-15 | EMRSA-16 | BB568 | USA300 | Mu50 | VRE1 | VRE10 |
| 16* | >32 | 32 | >32 | >32 | 32 | >32 | 16 |
| 18* | >32 | >32 | >32 | 32 | >32 | >32 | 16 |
| 26 | 0.06 | 0.125 | 0.125 | 0.125 | 0.06 | 0.06-0.125 | 0.06 |
| 27 | 0.03 | 0.125 | 0.125 | 0.06-0.125 | <0.03 | 0.125 | 0.03 |
| 28 | 0.06 | 0.125 | 0.125 | 0.06 | — | 0.06 | 0.06 |
| 30 | 0.5 | 2 | 2 | 0.5 | — | 1 | 0.5 |
| 31 | 0.5 | 4 | 4 | 1 | — | 1 | 0.5 |
| 35 | 0.06 | 0.06 | 0.06 | 0.06 | — | 0.06 | 0.06 |
| 37 | 0.125 | 0.5 | 0.5 | 0.125 | — | 0.25 | 0.125 |
| 39 | 0.25 | 0.25 | 0.25-0.5 | 0.5 | 0.125 | 0.125 | 0.5 |
| 40 | 0.125 | 0.5 | 0.5 | 0.125 | — | 0.25 | 0.125 |
| 49 | 2 | 2 | 2 | 2 | 1 | 0.5 | 0.5-1 |
| 51 | 2 | 2 | 2 | 2 | 1 | 0.5 | 1 |
| 52 | 4 | 1-2 | 4 | 4 | 2 | 2 | 1 |
| 53 | 1 | 2-4 | 4 | 4 | 2 | 1 | 0.5 |
| 54 | <0.03 | 0.06 | 0.125 | 0.06 | 0.03 | 0.06 | <0.03 |
| 56 | 0.25 | 0.5 | 0.5 | 1 | 0.5 | 0.5 | 0.25 |
| 59 | 2 | 16 | 16 | 16-32 | 4 | 32 | 4 |

*Comparative Examples

The invention claimed is:
1. A compound of formula I:

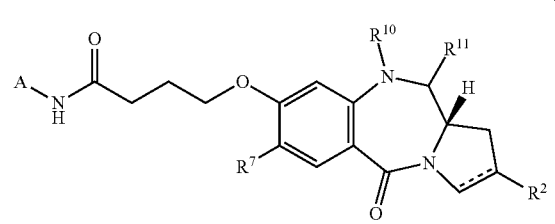

or a pharmaceutically acceptable salt thereof, wherein:
the dotted double bond indicates the presence of a single or double bond between C2 and C3;
R$^2$ is selected from —H, —OH, =O, =CH$_2$, —CN, —R, OR, halo, dihalo, =CHR, =CHRR', —O—SO$_2$—R, CO$_2$R and COR;
R$^7$ is selected from H, R, OH, OR, SH, SR, NH$_2$, NHR, NRR', nitro, Me$_3$Sn and halo;
where R and R' are independently selected from optionally substituted C$_{1-7}$ alkyl, C$_{2-7}$ alkenyl, C$_{2-7}$ alkynyl, C$_{3-7}$ cycloalkyl, C$_{3-20}$ heterocyclyl and C$_{5-20}$ aryl groups, wherein the optional substituents are selected from —F, —Cl, —Br, —I, —OH, —OR$^{24}$, —CH(OR$^{21}$)(OR$^{21}$), —CH(OH)(OR$^{21}$), —CR(OR$^{21}$)(OR$^{21}$), =O, =S, =NR$^{22}$, —C(=O)R$^{21}$, —C(=O)OH, —C(=S)SH, —C(=O)SH, —C(=S)OH, —C(=NH)OH, —C(=NOH)OH, —C(=O)OR²¹, —OC(=O)R²¹, —OC(=O)OR²¹, —NR²³R²³', —C(=O)NR²³R²³', —C(=S)NR²³R²³', —NR²²C(=O)R²¹, —OC(=O)NR²³R²³', —N(R²²)CONR²³R²³', —NH—C(=NH)NH₂, =NR²², —C(=NR²²)N(R²²)₂, —NO₂, —NO, —N₃, —CN, —NC, —OCN, —NCO, —SCN, —NCS, —SH, —SR²¹, —SS—R²¹, —S(=O)R²¹, —S(=O)R²¹, —S(=O)OH, —S(=O)₂OH, —S(=O)OR²¹, —S(=O)₂OR²¹, —OS(=O)R²¹, —OS(=O)R²¹, —OS(=O)₂OR²¹, —S(=O)NR²³R²³', —S(=O)₂NR²³R²³', —NR²²S(=O)₂OH, —NR²²S(=O)₂R²¹, —NR²²S(=O)R²¹, —PR²²₂, —P(=O)₂, —P(=O)(R²¹)₂, —P(=O)(OH)₂, —P(=O)(OR²²)₂, —OP(=O)(OH)₂, —OP(=O)(OR²²)₂, —OP(OH)₂, —OP(OR²²)₂, —OP(OR²²)—N(R²²)₂; and —OP(=O)(OR²²)—N(R²²)₂ wherein each R²¹ is independently selected from $C_{1-7}$ alkyl, a $C_{3-20}$ heterocyclyl, or a $C_{5-20}$ aryl;

each R²² is independently selected from hydrogen $C_{1-7}$ alkyl, a $C_{3-20}$ heterocyclyl or a $C_{5-20}$ aryl;

each R²³ is independently selected from hydrogen $C_{1-7}$ alkyl a $C_{3-20}$ heterocyclyl a $C_{5-20}$ or, in the case of a "cyclic" amino group, R²³ and R²³', taken together with the nitrogen atom to which they are attached, form a heterocyclic ring having from 4 to 8 ring atoms;

each R²⁴ is independently alkyl; and each R²⁵ is independently selected from optionally substituted $C_{1-7}$ alkyl a $C_{3-20}$ heterocyclyl, or a $C_{5-20}$ aryl;

R¹⁰ and R¹¹ either together form a double bond, or are selected from H and QR^Q respectively, where Q is selected from O, S and NH and R^Q is H or $C_{1-7}$ alkyl or H and $SO_xM$, where x is 2 or 3, and M is a monovalent pharmaceutically acceptable cation;

A is selected from A1, A2, A3, A4 or A5:

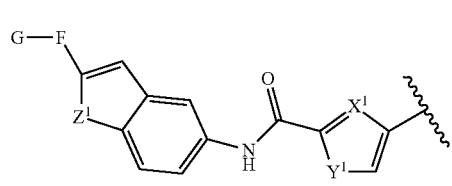
(A1)

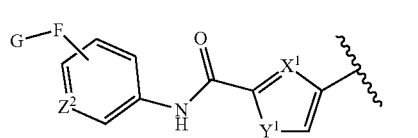
(A2)

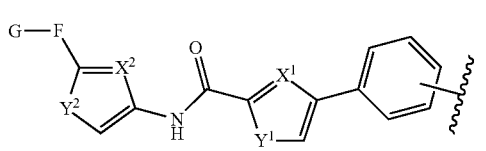
(A3)

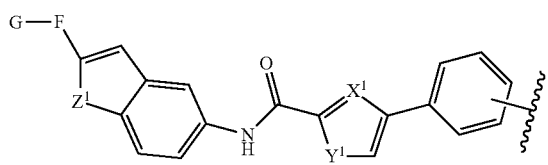
(A4)

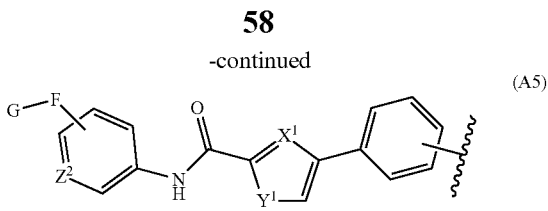
(A5)

Where
X¹ and Y¹ are selected from: CH and NH; CH and NMe; N and NMe; CH and S; N and S; N and O; and CH and O, respectively;

X² and Y² are selected from: CH and NH; CH and NMe; N and NMe; CH and S;
N and S; N and O; and CH and O, respectively;

Z¹ is selected from O and S;
Z² is selected from CH and N;
F is selected from a single bond and $-(E-F^1)_m-$;
each E is independently selected from a single bond, and —C(=O)—NH—;
each F¹ is independently a $C_{5-20}$ heteroarylene group;
m is 1, 2 or 3;
G is selected from hydrogen, $C_{1-4}$alkyl, —C(=O)—O—$C_{1-4}$alkyl, —(CH₂)ₙ—$C_{3-20}$ heterocyclyl, and —O—(CH₂)ₙ—$C_{3-20}$ heterocyclyl group;
each n is 0-4;
wherein $C_{3-20}$ heterocyclyl pertains to a monovalent moiety obtained by removing a hydrogen atom from a ring atom of a heterocyclic compound, which moiety has from 3 to 20 rings atoms, of which 1 to 10 are ring heteroatoms selected from N, O and S;
wherein $C_{5-20}$ heteroarylene pertains to a divalent moiety obtained by removing a hydrogen atom from each of two ring atoms of a heteroaromatic compound, which moiety has from 3 to 20 rings atoms, of which 1 to 10 are ring heteroatoms selected from N, O and S;
provided that A2 is not A2:

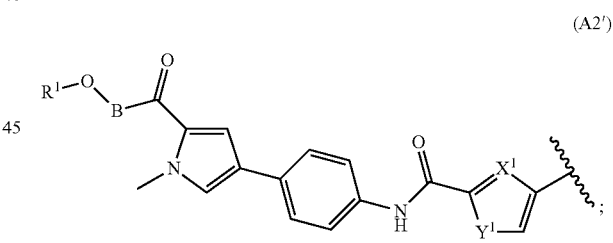
(A2')

where X¹ and Y¹ of A2' are selected from: CH and NMe; COH and NMe; CH and S; N and NMe; N and S, respectively; and
provided that A3 is not A3':

(A3')

where $X^2$ and $Y^2$ of A3' are selected from: CH and NMe; COH and NMe; CH and S; N and NMe; N and S, respectively;

B is either a single bond or:

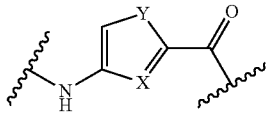
(B1)

where X and Y of B1 are selected from: CH and NMe; COH and NMe; CH and S; N and NMe; N and S, respectively; and $R^1$ is $C_{1-4}$ alkyl.

2. A compound according to claim 1, wherein $R^7$ is $OR^{7.4}$, where $R^{7.4}$ is optionally substituted $C_{1-7}$ alkyl.

3. A compound according to claim 2, wherein $R^{7.4}$ is selected from Me, $CH_2Ph$ and allyl.

4. A compound according to claim 1, wherein $R^{10}$ and $R^{11}$ form a double bond together.

5. A compound according to claim 1, wherein $R^1$ is $C_{1-2}$ alkyl.

6. A compound according to claim 5, wherein $R^1$ is methyl.

7. A compound according to claim 1, wherein $R^2$ is selected from —H, =$CH_2$, —R, =CHR, and =CRR'.

8. A compound according to claim 1, wherein $R^2$ is of the configuration C1:

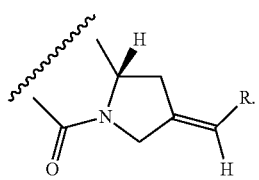
(C1)

9. A compound according to claim 1, wherein $R^2$ is selected from optionally substituted phenyl, optionally substituted napthyl, optionally substituted pyridyl, optionally substituted quinolinyl or isoquinolinyl.

10. A compound according to claim 9, wherein $R^2$ is selected from 4-methoxy-phenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthienyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl.

11. A compound according to claim 1, wherein $R^2$ is selected from:

(a) $C_{1-5}$ saturated aliphatic alkyl;
(b) $C_{3-6}$ saturated cycloalkyl;
(c)

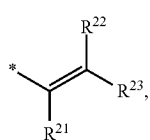

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(d)

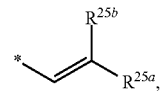

wherein one of $R^{25a}$ and $R^{25b}$ is H and the other is selected from:

phenyl, which phenyl is optionally substituted by a group selected from halo methyl, methoxy; pyridyl; and thiophenyl; and (e)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

12. A compound according to claim 1, wherein if $R^2$ is selected from =O, =$CH_2$, =CHR, =CHRR', there is a single bond between C2 and C3.

13. A compound according to claim 1, wherein there is no double bond between C2 and C3 and $R^2$ is H.

14. A compound according to claim 1, wherein $X^1$ and $Y^1$ are selected from N and NMe and CH and NMe, respectively.

15. A compound according to claim 1, wherein F is -(E-$F^1)_m$—, and $F^1$ is a $C_5$ heteroarylene group.

16. A compound according to claim 15, wherein $F^1$ is represented by structure F11:

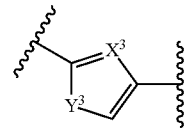 [SMILES: *c1coc(*)c1]
(F11)

wherein $X^3$ and $Y^3$ are selected from: CH and O; and CH and NMe, respectively.

17. A compound according to claim 1, wherein G is selected from the group consisting of —H, -Me, —C(=O)—O-Me, —$(CH_2)_n$—$N(CH_2CH_2OCH_2CH_2)$, and —O—$(CH_2)_n$—$N(CH_2CH_2OCH_2CH_2)$.

18. A compound according claim 1, wherein A is selected from the group consisting of:

wherein in A1:
$Z^1$ is O, $X^1$ is CH and $Y^1$ is NMe;
$Z^1$ is O, $X^1$ is N and $Y^1$ is NMe;
$Z^1$ is S, $X^1$ is CH and $Y^1$ is NMe; or
$Z^1$ is S, $X^1$ is N and $Y^1$ is NMe; and
wherein in A2:
$Z^1$ is CH, $X^1$ is CH and $Y^1$ is NMe;
$Z^1$ is N, $X^1$ is N and $Y^1$ is NMe;
$Z^1$ is CH, $X^1$ is N and $Y^1$ is NMe; or
$Z^1$ is N, $X^1$ is CH and $Y^1$ is NMe; and
wherein in A3:
$Y^1$ is NMe, $X^1$ is CH, $Y^2$ is NMe and $X^2$ is CH;
$Y^1$ is NMe, $X^1$ is CH, $Y^2$ is NMe and $X^2$ is N;
$Y^1$ is NMe, $X^1$ is N, $Y^2$ is NMe and $X^2$ is CH;

$Y^1$ is NMe, $X^1$ is N, $Y^2$ is NMe and $X^2$ is N;
$Y^1$ is O, $X^1$ is CH, $Y^2$ is NMe and $X^2$ is CH; or
$Y^1$ is O, $X^1$ is CH, $Y^2$ is NMe and $X^2$ is N; and
wherein in A4:
$Z^1$ is NMe, $X^1$ is CH and $Y^1$ is O; and
wherein in A5:
$Z^1$ is CH, $X^1$ is CH and $Y^1$ is NMe;
$Z^1$ is CH, $X^1$ is CH and $Y^1$ is O;
$Z^1$ is N, $X^1$ is CH and $Y^1$ is NMe; or
$Z^1$ is N, $X^1$ is CH and $Y^1$ is O.

19. A pharmaceutical composition comprising a compound according to claim 1, and a pharmaceutically acceptable carrier or diluent.

20. A method of treatment of a patient suffering from a bacterial infection, comprising administering to said patient a therapeutically acceptable amount of a compound according to claim 1.

\* \* \* \* \*